(12) United States Patent
Shin

(10) Patent No.: US 10,735,681 B2
(45) Date of Patent: Aug. 4, 2020

(54) INSPECTION DEVICE, IMAGE PROCESSING DEVICE, CORRECTION VALUE CALCULATING METHOD, IMAGE PROCESSING METHOD AND COMPUTER READABLE RECORDING MEDIUM

(71) Applicant: OLYMPUS CORPORATION, Tokyo (JP)

(72) Inventor: Hidetoshi Shin, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 211 days.

(21) Appl. No.: 15/972,713

(22) Filed: May 7, 2018

(65) Prior Publication Data

US 2018/0255258 A1 Sep. 6, 2018

Related U.S. Application Data

(63) Continuation of application No. PCT/JP2016/077338, filed on Sep. 15, 2016.

(30) Foreign Application Priority Data

Nov. 19, 2015 (JP) ................................. 2015-226806

(51) Int. Cl.
*H04N 5/365* (2011.01)
*H04N 5/378* (2011.01)
(Continued)

(52) U.S. Cl.
CPC ......... *H04N 5/3658* (2013.01); *A61B 1/0002* (2013.01); *A61B 1/00006* (2013.01);
(Continued)

(58) Field of Classification Search
CPC combination set(s) only.
See application file for complete search history.

(56) References Cited

U.S. PATENT DOCUMENTS 7,787,036 B2 * 8/2010 Egawa ................ H04N 5/3572
348/222.1
8,648,946 B2 2/2014 Morisaki et al.
(Continued)

FOREIGN PATENT DOCUMENTS

JP 2007-214775 A 8/2007
JP 2008-067060 A 3/2008
(Continued)

OTHER PUBLICATIONS

International Search Report dated Oct. 11, 2016 issued in PCT/JP2016/077338.
(Continued)

*Primary Examiner* — Janese Duley
(74) *Attorney, Agent, or Firm* — Scully, Scott, Murphy & Presser, P.C.

(57) ABSTRACT

An inspection device includes: an acquisition unit configured to acquire dark-time image data generated in a state where the imaging element is shielded from light; a first generation unit configured to generate average added image data by adding up the dark-time image data and dividing the added-up result by number of frames; a second generation unit configured to generate difference image data in which the average added image data is subtracted from the image data; a first calculation unit configured to calculate, as a lateral streak noise index, a statistical value of the difference image data; a second calculation unit configured to calculate the lateral streak noise indices; a third calculation unit configured to calculate, as the correction value, the correlation degree having a minimum value among the lateral streak noise indices; and a recording control unit configured to record the correction value in a recording unit.

13 Claims, 20 Drawing Sheets

(51) Int. Cl.
- *G02B 23/24* (2006.01)
- *A61B 1/00* (2006.01)
- *A61B 1/05* (2006.01)
- *H04N 5/232* (2006.01)
- *H04N 5/77* (2006.01)
- *A61B 1/045* (2006.01)
- *H04N 5/225* (2006.01)

(52) U.S. Cl.
CPC ............ *A61B 1/00009* (2013.01); *A61B 1/05* (2013.01); *G02B 23/2484* (2013.01); *H04N 5/232* (2013.01); *H04N 5/378* (2013.01); *H04N 5/772* (2013.01); *A61B 1/00025* (2013.01); *A61B 1/045* (2013.01); *H04N 2005/2255* (2013.01)

(56) References Cited

U.S. PATENT DOCUMENTS

| | | |
|---|---|---|
| 2008/0218615 A1 | 9/2008 | Huang et al. |
| 2009/0091641 A1 | 4/2009 | Hattori |
| 2012/0035419 A1* | 2/2012 | Ashida ............... A61B 1/00009 600/109 |
| 2013/0010166 A1 | 1/2013 | Morisaki et al. |

FOREIGN PATENT DOCUMENTS

| | | |
|---|---|---|
| JP | 2013-017040 A | 1/2013 |
| JP | 2013-150144 A | 8/2013 |
| WO | WO 2015/045486 A1 | 4/2015 |

OTHER PUBLICATIONS

Extended Supplementary European Search Report dated Jul. 4, 2019 in European Patent Application No. 16 86 6013.2.

* cited by examiner

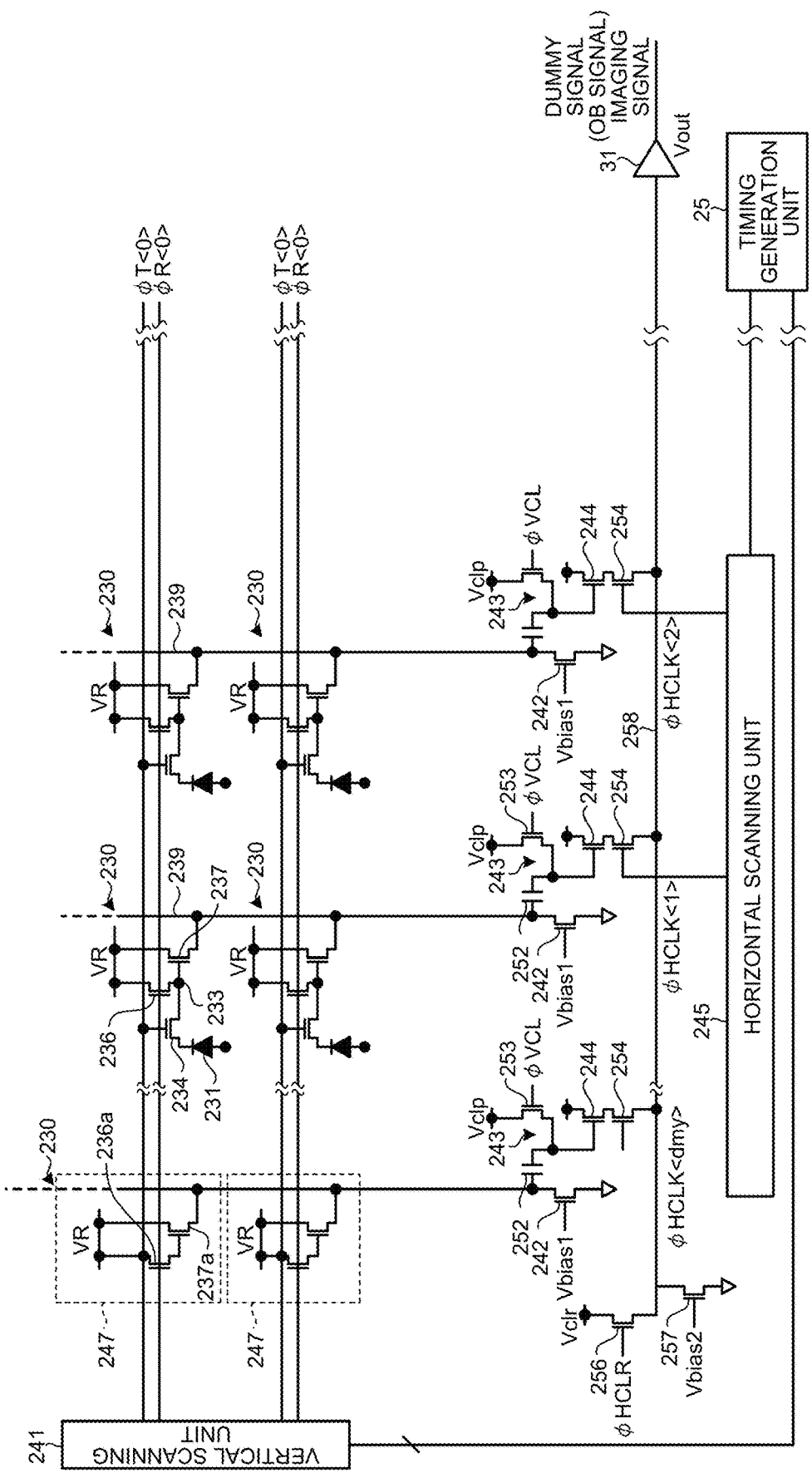

246a

246b

OB PIXEL REGION | EFFECTIVE PIXEL REGION

OB PIXEL REGION | EFFECTIVE PIXEL REGION

DUMMY PIXEL REGION — EFFECTIVE PIXEL REGION

P5$_{CIP}$

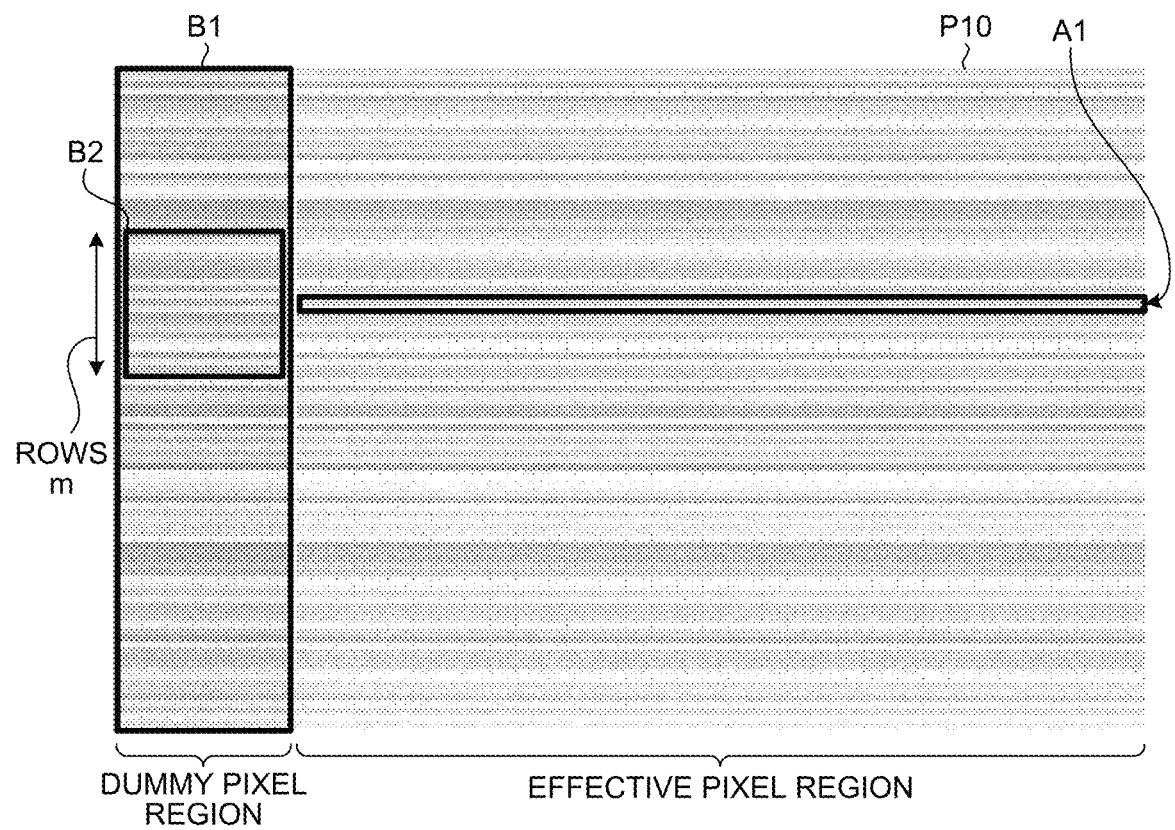

US 10,735,681 B2

INSPECTION DEVICE, IMAGE PROCESSING DEVICE, CORRECTION VALUE CALCULATING METHOD, IMAGE PROCESSING METHOD AND COMPUTER READABLE RECORDING MEDIUM

CROSS-REFERENCE TO RELATED APPLICATION

This application is a continuation of PCT International Application No. PCT/JP2016/077338 filed on Sep. 15, 2016 which claims the benefit of priority from Japanese Patent Application No. 2015-226806, filed on Nov. 19, 2015, the entire contents of which are incorporated herein by reference.

BACKGROUND

The present disclosure relates to an inspection device, an image processing device, a correction value calculating method, an image processing method, and a computer readable recording medium.

In recent years, an imaging device such as a digital camera includes an imaging element such as a complementary metal oxide semiconductor (CMOS) sensor or a charge coupled device (CCD) sensor. In image data generated by such an imaging element, lateral streak noise is generated due to fluctuation in power supply voltage, capturing of a subject with high luminance, or the like. As a method of correcting such lateral streak noise, there is a known technology in which an offset value is calculated by subtracting a reference black level from an average value of output signals in an OB pixel portion formed of a plurality of photodiodes shielded from light, and after that, a correction amount is calculated by multiplying the offset value by a coefficient defined by a structure of an imaging element, and then a signal of an effective pixel portion formed of a plurality of photodiodes not shielded from light is corrected based on the correction amount (refer to JP 2008-67060 A).

SUMMARY

An inspection device according to one aspect of the present disclosure for calculating a correction value to correct lateral streak noise included in image data generated by an imaging element that includes: a plurality of effective pixels arranged in a two-dimensional matrix, each receiving light from outside, and generating and outputting an imaging signal in accordance with a received light amount; and one or a plurality of correction pixels provided in each horizontal line in arrangement of the plurality of effective pixels, and generating and outputting a dummy signal used in correction processing for the imaging signal, includes: an acquisition unit configured to acquire, from the imaging element, a plurality of pieces of dark-time image data generated by the imaging element in a state where the imaging element is shielded from light; a first generation unit configured to generate average added image data by adding up the plurality of pieces of dark-time image data acquired by the acquisition unit and dividing the added-up result by number of frames of the dark-time image data; a second generation unit configured to generate, for each frame, difference image data in which the average added image data generated by the first generation unit is subtracted from the image data corrected based on a correlation degree between the plurality of correction pixels and the plurality of effective pixels in each horizontal line; a first calculation unit configured to calculate, as a lateral streak noise index, a statistical value of the difference image data generated by the second generation unit for each frame; a second calculation unit configured to calculate, for each correlation degree, a plurality of the lateral streak noise indices calculated by the first calculation unit for each frame; a third calculation unit configured to calculate, as the correction value, the correlation degree having a minimum value among the plurality of lateral streak noise indices calculated by the second calculation unit for each correlation degree; and a recording control unit configured to record the correction value calculated by the third calculation unit in a recording unit provided in the imaging element.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 4 is a circuit diagram illustrating a configuration of the first chip;

FIG. 10 is a view schematically illustrating a method of calculating a clamp value executed by the inspection device according to the first embodiment;

DETAILED DESCRIPTION

Figure 1:
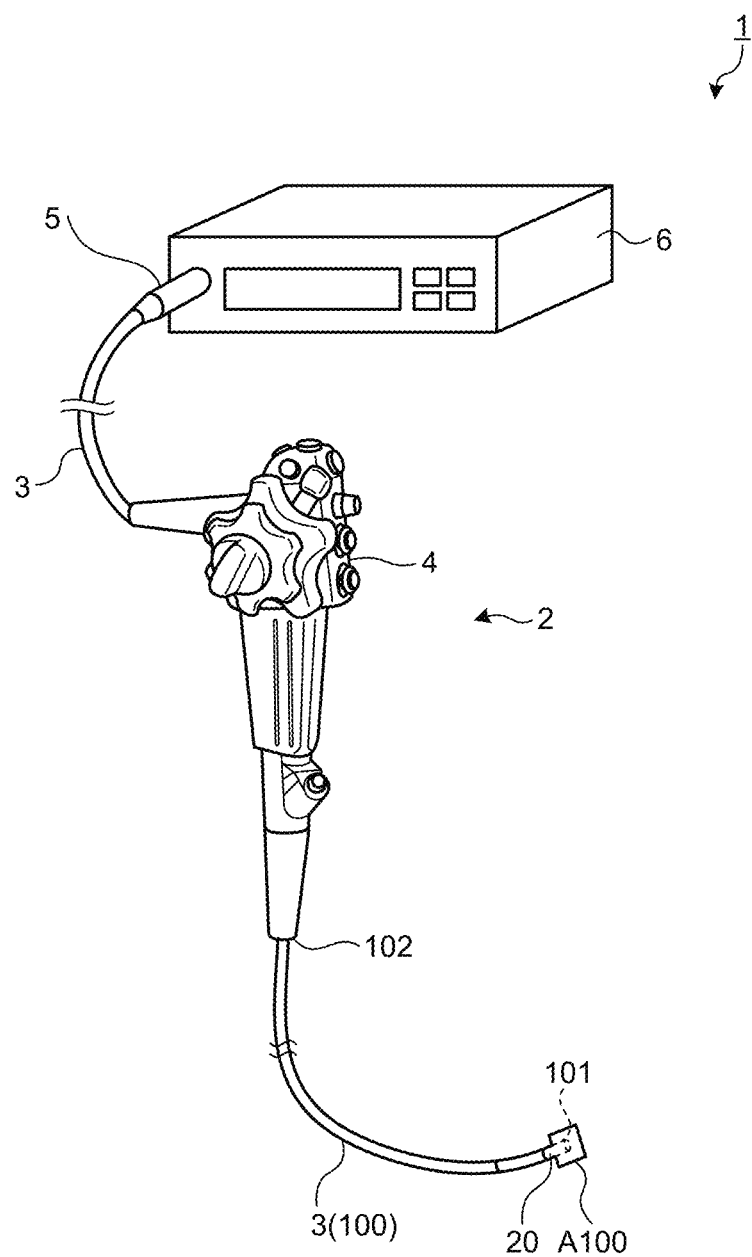
FIG. 1 is a view schematically illustrating an entire structure of an inspection system according to a first embodiment.

In the following, an inspection system and an endoscope system to inspect an image taken by an endoscope (imaging device) including an imaging element such as a CMOS or CCD will be described as modes to implement the present disclosure (hereinafter referred to as "embodiments"). Additionally, note that the present disclosure is not limited by the embodiments. Furthermore, note that the description will be provided by denoting a same component by a same reference sign in the drawings. Moreover, it is necessary to consider that the drawings are schematically illustrated and a relation between a thickness and a width of respective members, a proportion of each member, and the like may differ from those used in practice. Additionally, note that the drawings may include portions having sizes or proportions different from each other.

First Embodiment

Structure of Inspection System

FIG. 1 is a diagram schematically illustrating an entire structure of an inspection system according to a first embodiment. An inspection system 1 illustrated in FIG. 1 includes an endoscope 2 and an inspection device 6.

The endoscope 2 includes a transmission cable 3, an operating unit 4, and a connector portion 5. The endoscope 2 captures an in-vivo image of a subject by inserting an inserting portion 100 that is a part of the transmission cable 3 into a body cavity of the subject, and outputs an imaging signal (image data) to the inspection device 6 or a processor (image processing device) described later. Additionally, the endoscope 2 includes: an imaging unit 20 (imaging device) that captures an in-vivo image and is located on one end of the transmission cable 3, that is, a distal end 101 side of the inserting portion 100 to be inserted into a body cavity of a subject; and an operating unit 4 that is located on a proximal end 102 side of the inserting portion 100 and receives various kinds of operation for the endoscope 2.

The imaging unit 20 is connected to the connector portion 5 via the operating unit 4 by the transmission cable 3. Image data captured by the imaging unit 20 is output to the connector portion 5 via the transmission cable 3 having a length of several meters, for example. Furthermore, a light shielding cap A100 is detachably provided at the distal end 101. The light shielding cap A100 is used when the endoscope 2 generates a dark-time image. Here, the dark-time image is an image (image data) generated without light receiving by an imaging element of the imaging unit 20 described later.

The connector portion 5 is connected to the inspection device 6 or the processor described later, applies predetermined signal processing to an imaging signal output from the imaging unit 20, also applies A/D conversion to the imaging signal to convert the same from an analog signal to a digital signal, and outputs the digital signal to the inspection device 6 or the processor.

The inspection device 6 calculates a correction amount and a coefficient in order to correct lateral streak noise included in an imaging signal generated by the endoscope 2, and records these calculation results in the endoscope 2.

Figure 2:
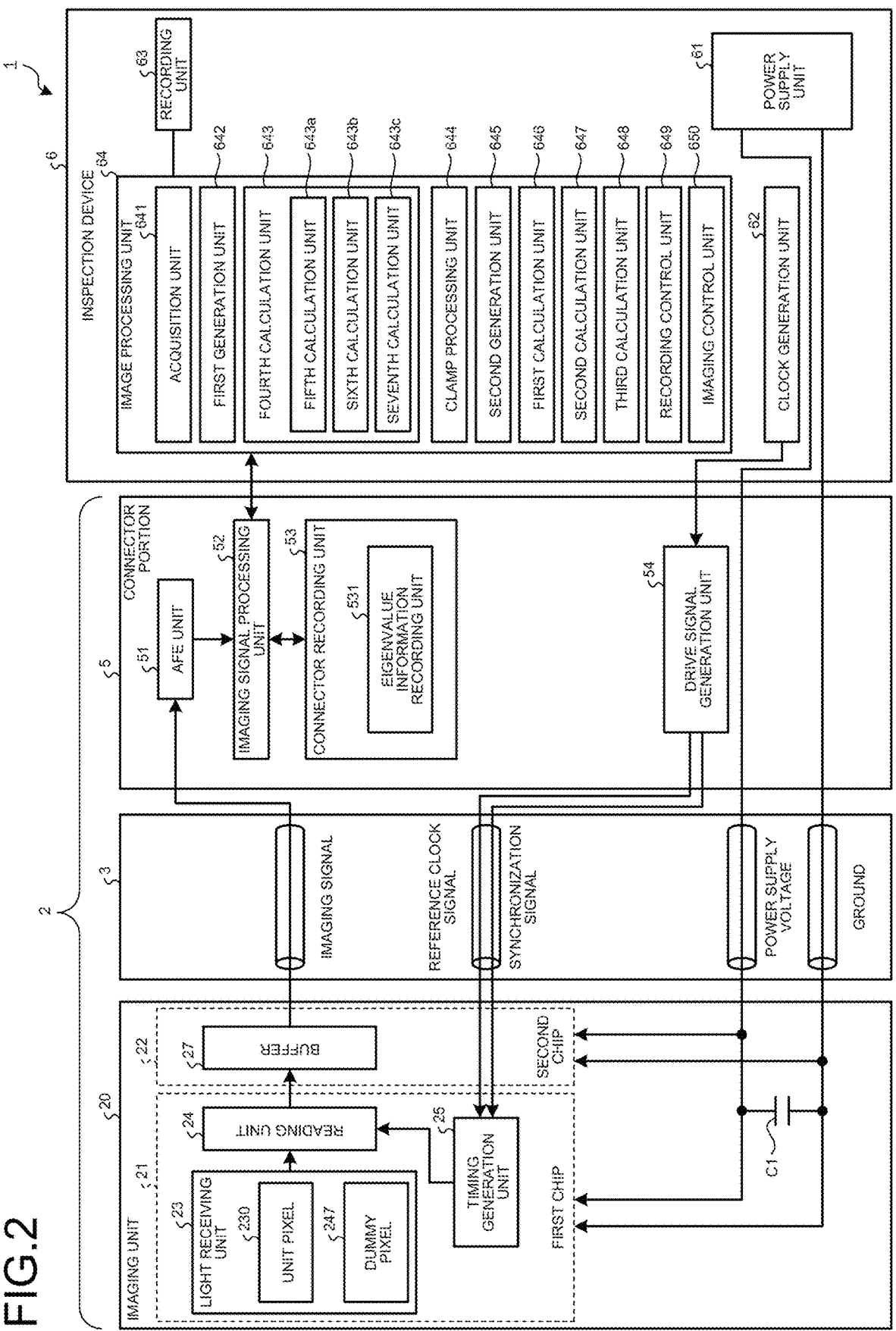
FIG. 2 is a block diagram illustrating functions of a main portion of the inspection system according to the first embodiment.

FIG. 2 is a block diagram illustrating functions of a main portion of the inspection system 1. Details of respective components of the inspection system 1 and a channel of an electric signal inside the inspection system will be described with reference to FIG. 2.

Configuration of Endoscope

As illustrated in FIG. 2, the endoscope 2 includes the imaging unit 20, transmission cable 3, and connector portion 5. The imaging unit 20 includes a first chip 21 (imaging element) and a second chip 22.

The first chip 21 includes: a light receiving unit 23 having a plurality of unit pixels 230 that is arranged in a two-dimensional matrix in a matrix direction, each receives light from the outside, and each generates and outputs an imaging signal in accordance with a received light amount, and a plurality of dummy pixels 247 that is provided in each vertical line in arrangement of the plurality of unit pixels 230 and each generates and outputs a dummy signal to be used in correction processing for an imaging signal; a reading unit 24 that reads an imaging signal and a dummy signal photoelectrically converted in the light receiving unit 23; and a timing generation unit 25 that generates a timing signal based on a reference clock signal and a synchronization signal received from the connector portion 5, and outputs the generated timing signal to the reading unit 24. Note that a more detailed configuration of the first chip 21 will be described later with reference to FIG. 3.

The second chip 22 has a buffer 27 that functions as a transmission unit to transmit an imaging signal output from the first chip 21 to the inspection device 6 or the processor described later via the transmission cable 3 and the connector portion 5. Note that combination of circuits mounted on the first chip 21 and the second chip 22 may be suitably changed in accordance with setting convenience.

Additionally, the imaging unit 20 receives, together with ground GND, power supply voltage VDD generated by a power supply unit 61 inside the inspection device 6 or a power supply unit of the processor described later via the transmission cable 3. A capacitor C1 for power supply stabilization is provided between the power supply voltage VDD and the ground GND which are supplied to the imaging unit 20.

The connector portion 5 includes an analog front end unit 51 (hereinafter referred to as "AFE unit 51"), an imaging signal processing unit 52, a connector recording unit 53, and a drive signal generation unit 54. The connector portion 5 electrically connects the endoscope 2 (imaging unit 20) to a processor 9 and functions as a relay processing unit to relay an electric signal. The connector portion 5 and the imaging unit 20 are connected by the transmission cable 3, and the connector portion 5 and the processor 9 are connected by, for example, a coil cable.

The AFE unit 51 receives an imaging signal output from the imaging unit 20 via the transmission cable 3, performs impedance matching with a passive element such as a resistance, and extracts an AC component at a capacitor, and then determines an operating point in a voltage-dividing resistance. After that, the AFE unit 51 applies analog-digital (A/D) conversion to an analog imaging signal, and transmits the converted signal to the imaging signal processing unit 52 as a digital imaging signal.

The imaging signal processing unit 52 is formed of, for example, a field programmable gate array (FPGA), and generates a reference clock signal (e.g., a clock signal of 27 MHz) to be a reference of operation in respective components of the endoscope 2, and a synchronization signal indicating a start position of each frame, supplies the generated signals to the timing generation unit 25, applies predetermined signal processing such as noise removal to a digital imaging signal received from the AFE unit 51, and outputs the same to inspection device 6 or the processor described later.

The connector recording unit 53 is formed by using a flash memory, a random access memory (RAM), or the like, and temporarily records: various kinds of information to drive the endoscope 2; and parameters in processing. Furthermore, the connector recording unit 53 includes an eigenvalue information recording unit 531 to record an eigenvalue calculated by the inspection device 6 described later and used in correcting lateral streak noise.

The drive signal generation unit 54 generates a synchronization signal indicating a start position of each frame based on a reference clock signal (e.g., clock signal of 27 MHz) that is supplied from the inspection device 6 and serves as a reference of operation in respective components of the endoscope 2, and outputs the synchronization signal together with the reference clock signal to the timing generation unit 25 of the imaging unit 20 via the transmission cable 3. Here, the synchronization signal generated by the drive signal generation unit 54 includes a horizontal synchronization signal and a vertical synchronization signal.

Configuration of Inspection Device

Next, a detailed configuration of the inspection device 6 will be described. The inspection device 6 includes a power supply unit 61, a clock generation unit 62, a recording unit 63, and an image processing unit 64.

The power supply unit 61 generates power supply voltage VDD and supplies the generated power supply voltage VDD to the imaging unit 20 together with ground GND via the connector portion 5 and the transmission cable 3.

The clock generation unit 62 generates a reference clock signal and outputs the generated reference clock signal to the drive signal generation unit 54.

The recording unit 63 is formed by using a flash memory, a random access memory (RAM), or the like, and temporarily records: various kinds of information to drive the inspection device 6; and parameters in processing. Additionally, the recording unit 63 sequentially records an imaging signal generated by the imaging unit 20 of the endoscope 2.

The image processing unit 64 includes an acquisition unit 641, a first generation unit 642, a fourth calculation unit 643, a clamp processing unit 644, a second generation unit 645, a first calculation unit 646, a second calculation unit 647, a third calculation unit 648, a recording control unit 649, and an imaging control unit 650.

The acquisition unit 641 acquires, from the imaging unit 20, a plurality of pieces of dark-time image data generated by the imaging unit 20 of the endoscope 2 via the connector portion 5 of the endoscope 2 in state that the imaging unit (imaging element) 20 is shielded from light.

The first generation unit 642 adds up the plurality of pieces of dark-time image data acquired by the acquisition unit 641, and generates average added image data by dividing the added-up data by the number of frames of the dark-time image data. Specifically, the first generation unit 642 adds up all of the plurality of pieces of dark-time image data acquired by the acquisition unit 641 and generates the average added image data by dividing an added-up result by the number of frames of the dark-time image data.

The fourth calculation unit 643 calculates, for each horizontal line, a clamp value in order to correct an imaging signal of each of the plurality of unit pixels 230 based on a correlation degree between the plurality of dummy pixels 247 and the plurality of unit pixels 230 in each horizontal line. Specifically, the fourth calculation unit 643 adds weights to the plurality of dummy pixels 247 in each horizontal line based on the correlation degree with the plurality of unit pixels 230, and calculates, for each horizontal line, a clamp value in order to correct an imaging signal of each of the plurality of unit pixels 230. The fourth calculation unit 643 includes a fifth calculation unit 643a, a sixth calculation unit 643b, and a seventh calculation unit 643c.

The fifth calculation unit 643a calculates, for each frame, an average value of dummy signals respectively output from the plurality of dummy pixels 247 in a dark-time image corresponding to dark-time image data acquired by the acquisition unit 641.

The sixth calculation unit 643b calculates an average value of dummy signals respectively output from the plurality of dummy pixels 247 in a range of horizontal lines which include a horizontal line to be corrected in the dark-time image corresponding to the dark-time image data acquired by the acquisition unit 641 and are located in a vertical direction while setting the horizontal line as a reference.

The seventh calculation unit 643c calculates a clamp value based on: a horizontal line to be corrected; a range of horizontal lines; an average value of dummy signals respectively output from a plurality of dummy pixels 247 in a dark-time image; an average value of dummy signals respectively output from the plurality of dummy pixels 247 in the range of horizontal lines; and a coefficient indicating a correlation degree. Specifically, the seventh calculation unit 643c calculates a clamp value based on: a horizontal line to be corrected, a range of horizontal lines; an average value of dummy signals respectively output from a plurality of dummy pixels 247 in a dark-time image; an average value of dummy signals respectively output from the plurality of dummy pixels 247 in the range of horizontal lines; and weighting in accordance with a coefficient indicating a correlation degree.

The clamp processing unit 644 performs, for each horizontal line, clamp processing to subtract a clamp value calculated by the fourth calculation unit 643 from an imaging signal of each of the plurality of unit pixels 230.

The second generation unit 645 generates, for each frame, difference image data obtained by subtracting average added image data generated by the first generation unit 642 from image data corrected by weighting based on a correlation degree between a plurality of dummy pixels 247 and a plurality of unit pixels 230 in each horizontal line of the imaging unit 20. Specifically, the second generation unit 645 generates, for each frame, difference image data by subtracting average added image data generated by the first generation unit 642 from image data subjected to the clamp processing by the clamp processing unit 644. Here, the correlation degree represents a difference between a dummy signal output from each of the plurality of dummy pixels 247 and an imaging signal output from each of the plurality of unit pixels 230 in each horizontal line.

The first calculation unit 646 calculates, as a lateral streak noise index, a statistical value of difference image data in each frame generated by the second generation unit 645. Specifically, the first calculation unit 646 calculates any one of an average value, a median value, a maximum value, a minimum value, and a mode of imaging signals in each horizontal line of a difference image corresponding to difference image data generated by the second generation unit 645. Note that a description will be provided below assuming that the first calculation unit 646 calculates an average value of imaging signals in each horizontal line of a difference image corresponding to difference image data generated by the second generation unit 645.

The second calculation unit 647 calculates, for each correlation degree between the plurality of dummy pixels 247 and the plurality of unit pixels 230 in each horizontal line of the imaging unit 20, a plurality of lateral streak noise indices calculated by the first calculation unit 646 for each frame. Specifically, the second calculation unit 647 calculates, as a lateral streak noise index for each frame, a statistical value based on an average value of imaging signals calculated by the first calculation unit 646 for each horizontal line.

The third calculation unit 648 calculates, as a correction value to correct lateral streak noise included in image data, a correlation degree between the plurality of dummy pixels 247 and the plurality of unit pixels 230 in each horizontal line of the imaging unit 20, in which the correlation degree has a minimum value among the plurality of lateral streak noise indices calculated by the second calculation unit 647 for each correlation degree between the plurality of dummy pixels 247 and the plurality of unit pixels 230 in each horizontal line of the imaging unit 20.

The recording control unit 649 records the correction value calculated by the third calculation unit 648 in the eigenvalue information recording unit 531 of the connector recording unit 53 in the endoscope 2.

The imaging control unit 650 controls imaging operation of the endoscope 2 connected to the inspection device 6. Specifically, the imaging control unit 650 causes the endoscope 2 connected to the inspection device 6 to start imaging at a predetermined frame rate.

Configuration of First Chip

Next, a detailed configuration of the above-described first chip 21 will be described.

Figure 3:
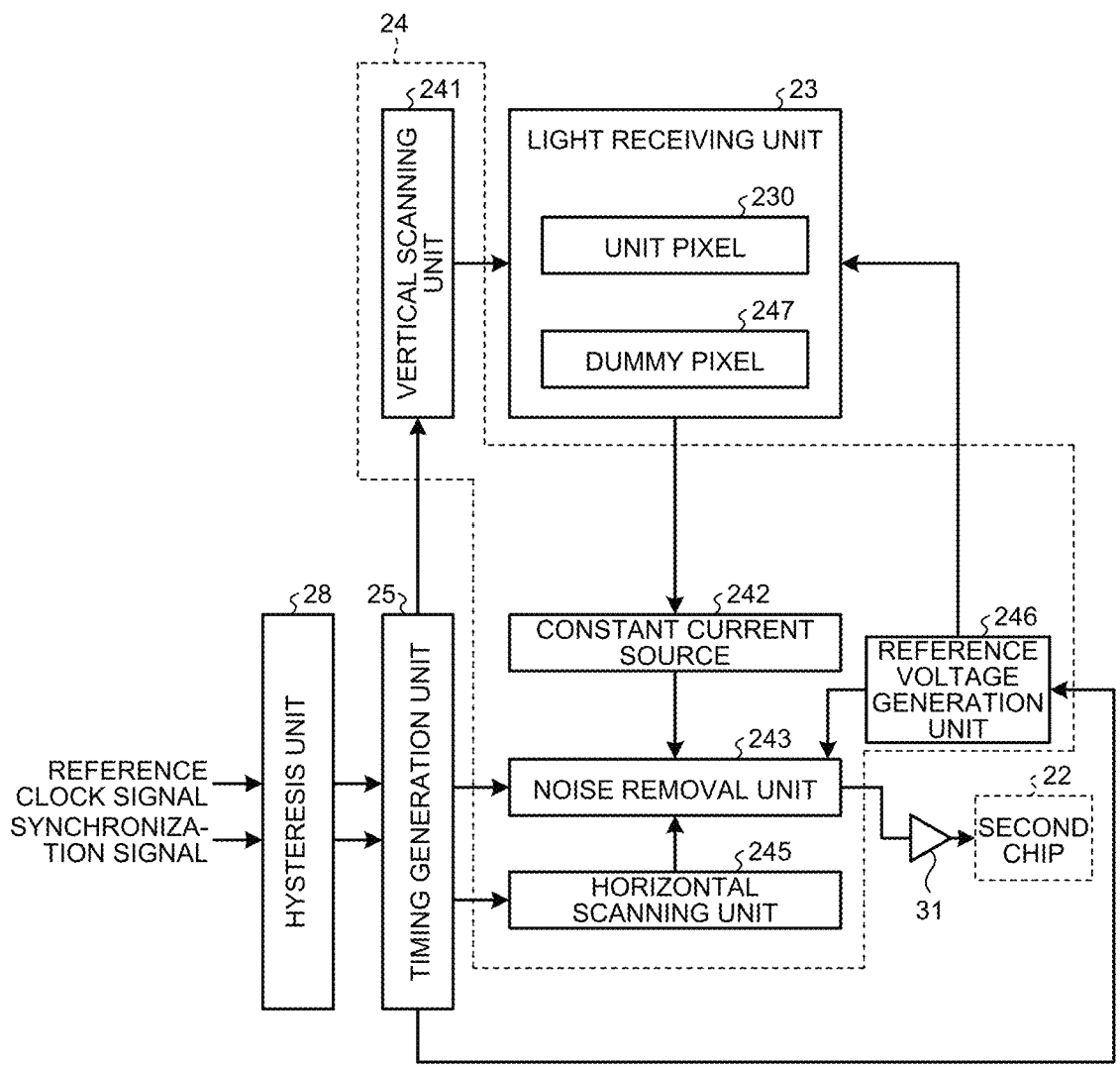
FIG. 3 is a block diagram illustrating a detailed configuration of a first chip illustrated in FIG. 2.

FIG. 3 is a block diagram illustrating the detailed configuration of the first chip illustrated in FIG. 2. FIG. 4 is a circuit diagram illustrating a configuration of the first chip 21.

As illustrated in FIGS. 3 and 4, the first chip 21 includes the light receiving unit 23, the reading unit 24 (driving unit), the timing generation unit 25, a hysteresis unit 28, and an output unit 31 (amplifier).

The hysteresis unit 28 shapes waveforms of a reference clock signal and a synchronization signal received via the transmission cable 3 and outputs, to the timing generation unit 25, the reference clock signal and the synchronization signal subjected to the waveform shaping.

The timing generation unit 25 generates various kinds of drive signals based on the reference clock signal and the synchronization signal received from the hysteresis unit 28, and outputs the drive signals respectively to a vertical scanning unit 241 (row selection circuit), a noise removal unit 243, and a horizontal scanning unit 245 of the reading unit 24 described later.

The reading unit 24 transfers, to the output unit 31, an imaging signal output from each of the plurality of pixels of the light receiving unit 23 described later and a reference signal output from a reference voltage generation unit 246.

Here, a detailed configuration of the reading unit 24 will be described. The reading unit 24 includes the vertical scanning unit 241 (row selection circuit), a constant current source 242, the noise removal unit 243 (noise removal circuit), a column source follower transistor 244, the horizontal scanning unit 245, and the reference voltage generation unit 246.

The vertical scanning unit 241 drives each of the unit pixels 230 and dummy pixels 247 of the light receiving unit 23 with the constant current source 242 by applying drive signals $\phi T<M>$ and $\phi R<M>$ to a selected row (horizontal line) $<M>$ (M=0, 1, 2 . . . , m−1, m) of the light receiving unit 23 based on drive signals ($\phi T$, $\phi R$, and the like) received from the timing generation unit 25, thereby transferring, to a vertical transfer line 239 (first transfer line), an imaging signal, a dummy signal, and a noise signal at the time of pixel resetting, and then outputting the same to the noise removal unit 243.

The noise removal unit 243 removes non-uniform output of the respective unit pixels 230 and the noise signal at the time of pixel resetting, and outputs an imaging signal photoelectrically converted in each of the unit pixels 230. Note that details of the noise removal unit 243 will be described later.

The horizontal scanning unit 245 applies a drive signal $\phi HCLK<N>$ to a selected column (vertical line) $<N>$ (N=0, 1, 2, . . . , n−1, n) of the light receiving unit 23 based on a drive signal ($\phi HCLK$) supplied from the timing generation unit 25, and transfers an imaging signal photoelectrically converted in each of the unit pixels 230 to a horizontal transfer line 258 (second transfer line) via the noise removal unit 243, and then outputs this image signal to the output unit 31. Note that, in the first embodiment, the horizontal transfer line 258 functions as a transfer unit that transfers an imaging signal output from each of the unit pixels 230.

In the light receiving unit 23 of the first chip 21, a large number of unit pixels 230 are arranged in a two-dimensional matrix. Each of the unit pixels 230 includes: a photoelectric conversion element 231 (photodiode), a charge converter 233, a transfer transistor 234 (first transfer unit), a pixel reset unit 236 (transistor), a pixel source follower transistor 237, and a dummy pixel 247 (reference signal generation unit). Note that, in the present specification, one or a plurality of photoelectric conversion elements and a transfer transistor to transfer signal charge from each of the photoelectric conversion elements to the charge converter 233 are referred to as a unit cell. In other words, a unit cell includes a set formed of one or a plurality of photoelectric conversion elements and a transfer transistor, and one unit cell is included in each of the unit pixels 230.

The photoelectric conversion element 231 photoelectrically converts incident light into a signal charge amount in accordance with a light amount, and accumulates the signal charge. Each of the photoelectric conversion element 231 has a cathode connected to one end of the transfer transistor 234 and an anode connected to the ground GND. The charge converter 233 is formed of a floating diffusion capacitance (FD), and converts the charge accumulated in the photoelectric conversion element 231 into voltage.

The transfer transistor 234 transfers the signal charge from the photoelectric conversion element 231 to the charge converter 233. The transfer transistor 234 has a gate connected to a signal line supplied with a drive signal (row selection pulse) φR and a drive signal φT, and the other end connected to the charge converter 233. When the drive signal φR and the drive signal φT are supplied from the vertical scanning unit 241 via the signal line, the transfer transistor 234 is turned on and transfers the signal charge from the photoelectric conversion element 231 to the charge converter 233.

The pixel reset unit 236 resets the charge converter 233 to a predetermined potential. The pixel reset unit 236 has one end connected to power supply voltage VR, and the other end connected to the charge converter 233, and a gate connected to a signal line supplied with the drive signal φR. When the drive signal φR is supplied from the vertical scanning unit 241 via the signal line, the pixel reset unit 236 is turned on, releases the signal charge accumulated in the charge converter 233, and resets the charge converter 233 to the predetermined potential.

The pixel source follower transistor 237 has one end connected to the power supply voltage VR, the other end connected to the vertical transfer line 239, and a gate in which a signal (imaging signal or signal at the time of resetting) converted to voltage by the charge converter 233 is received. When the drive signal φT is supplied to the gate of the transfer transistor 234 after selecting operation described later, charge is read from the photoelectric conversion element 231 and converted to voltage by the charge converter 233, and the pixel source follower transistor 237 has the charge transferred to the vertical transfer line 239.

A plurality of dummy pixels 247 is provided in each horizontal line of unit pixels 230. Note that, in FIG. 4, an example in which one dummy pixel 247 is provided in each horizontal line is illustrated to simplify the description, but not limited thereto, the number of dummy pixels 247 may be suitably changed. Each of the dummy pixels 247 includes a pixel reset unit 236a and a pixel source follower transistor 237a. In other words, the dummy pixel 247 has a configuration omitting, from the unit pixel 230, the photoelectric conversion element 231 (photodiode), the charge converter 233, and the transfer transistor 234 (first transfer unit).

The pixel reset unit 236a fixes the gate of the pixel source follower transistor 237a at a predetermined potential. The pixel reset unit 236a has one end connected to the power supply voltage VR, the other end connected to the gate of the pixel source follower transistor 237a, and a gate connected to a signal line supplied with the drive signal φT and the drive signal φR.

When the drive signal φR is supplied from the timing generation unit 25 to the gate of the pixel reset unit 236a via the signal line, the pixel reset unit 236a is turned on, and the gate of the pixel source follower transistor 237a is fixed at the predetermined potential (VR).

The pixel source follower transistor 237a has one end connected to the power supply voltage VR supplied from the reference voltage generation unit 246 (reference voltage generation unit 246a illustrated in FIG. 5A), the other end connected to the vertical transfer line 239, and a gate in which the predetermined potential (VR) is received. In the pixel source follower transistor 237a thus configured, when selecting operation described later is performed, a dummy signal (equivalent to an OB signal) according to the predetermined potential VR is transferred to the vertical transfer line 239 via the pixel source follower transistor 237a.

Similar to a normal unit pixel 230, in the first embodiment, in a case where the drive signal φR is supplied to the gate of the pixel reset unit 236a when the power supply voltage VR is applied at a level of the power supply voltage VDD (e.g., 3.3 V) and VR (e.g., 2 V), the pixel source follower transistor 237a is turned on, and the dummy pixel 247 including the pixel reset unit 236a is selected (selecting operation). Additionally, in a case where the drive signal φR is supplied to the gate of the pixel reset unit 236a when the power supply voltage VR is applied at a non-selection voltage level (e.g., 1 V) and VR (e.g., 1 V), the pixel source follower transistor 237a is turned off, and selection of the dummy pixel 247 including the pixel reset unit 236a is canceled (non-selecting operation).

The constant current source 242 has one end connected to the vertical transfer line 239, the other end connected to the ground GND, and a gate applied with bias voltage Vbias1. The constant current source 242 drives the unit pixel 230 with the constant current source 242, and reads output of the unit pixel 230 to the vertical transfer line 239. A signal read to the vertical transfer line 239 is received in the noise removal unit 243.

The noise removal unit 243 includes a transfer capacitance 252 (AC coupling capacitor) and a clamp switch 253 (transistor).

The transfer capacitance 252 has one end connected to the vertical transfer line 239 and the other end connected to the column source follower transistor 244.

The clamp switch 253 has one end connected to a signal line supplied with clamp voltage Vclp from the reference voltage generation unit 246. The clamp switch 253 has the other end connected between the transfer capacitance 252 and the column source follower transistor 244, and has a gate in which a drive signal φVCL is received from the timing generation unit 25. An imaging signal received in the noise removal unit 243 is an optical noise sum signal including a noise component.

When the drive signal φVCL is received in the gate of the clamp switch 253 from the timing generation unit 25, the clamp switch 253 is turned on, and the transfer capacitance 252 is reset by the clamp voltage Vclp supplied from the reference voltage generation unit 246. An imaging signal having noise removed by the noise removal unit 243 is received in the gate of the column source follower transistor 244.

Since the noise removal unit 243 does not require a sampling capacitor (sampling capacitance), the transfer capacitance (AC coupling capacitor) 252 is only to have a sufficient capacitance for a receiving capacitance of the column source follower transistor 244. Furthermore, an area occupied by the noise removal unit 243 may be reduced in the first chip 21 because a sampling capacitance may be omitted.

The column source follower transistor 244 has one end connected to the power supply voltage VDD, the other end connected to one end of a column selection switch 254 (second transfer unit), and the gate in which an imaging signal having noise removed by the noise removal unit 243 is received.

The column selection switch 254 has one end connected to the other end of the column source follower transistor 244, has the other end connected to the horizontal transfer line 258 (second transfer line), and has a gate connected to a signal line to be supplied a drive signal φHCLK<M> from the horizontal scanning unit 245. When the drive signal φHCLK<M> is supplied from the horizontal scanning unit 245 to the gate of the column selection switch 254 of a column <M>, the column selection switch 254 is turned on, and transfers a signal of the vertical transfer line 239 in the column <M> (an imaging signal having noise removed by the noise removal unit 243) to the horizontal transfer line 258.

A horizontal reset transistor 256 has one end connected to the ground GND, the other connected to the horizontal transfer line 258, and a gate in which a drive signal φHCLR is received from the timing generation unit 25. When the drive signal φHCLR is received from the timing generation unit 25 in the gate of the horizontal reset transistor 256, the horizontal reset transistor 256 is turned on and resets the horizontal transfer line 258.

A constant current source 257 has one end connected to the horizontal transfer line 258, the other end connected to the ground GND, and a gate applied with bias voltage Vbias2. The constant current source 257 reads an imaging signal from the vertical transfer line 239 to the horizontal transfer line 258. The imaging signal or a dummy signal read to the horizontal transfer line 258 is received in the output unit 31.

The output unit 31 amplifies and outputs an imaging signal having noise removed and a dummy signal (reference signal to be a reference at the time of correcting a lateral line) as needed (Vout).

In the first embodiment, crosstalk of an imaging signal in a column direction may be suppressed by alternately performing reading of an imaging signal after noise removal from the vertical transfer line 239 and resetting of the horizontal transfer line 258 by the horizontal reset transistor 256.

In the second chip 22, a dummy signal and an imaging signal are transmitted to the connector portion 5 via the transmission cable 3.

Figure 5A:
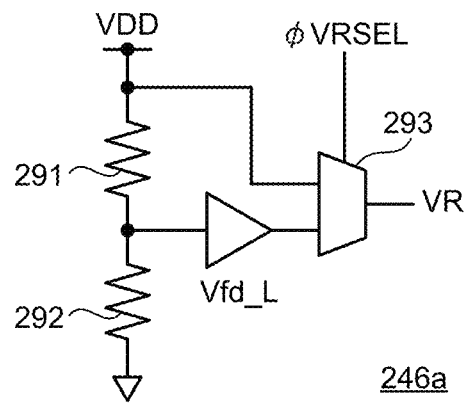
FIG. 5A is a circuit diagram illustrating a configuration of a reference voltage generation unit of a light receiving unit of an endoscope according to the first embodiment.
Figure 5B:
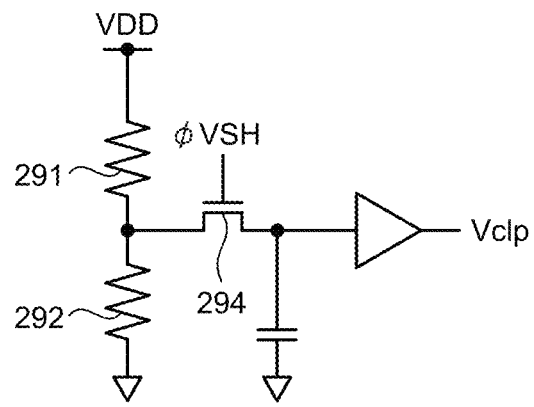
FIG. 5B is a circuit diagram illustrating a configuration of the reference voltage generation unit of the light receiving unit of the endoscope according to the first embodiment.

FIGS. 5A and 5B are circuit diagrams illustrating configurations of the reference voltage generation unit 246 of the light receiving unit 23 of the endoscope 2 according to the first embodiment.

A reference voltage generation unit 246a illustrated in FIG. 5A includes: a resistance voltage dividing circuit including two resistances 291 and 292; and a multiplexer 293 driven by a drive signal φVRSEL.

The multiplexer 293 alternately switches the power supply voltage VDD (e.g., 3.3 V) and non-selection voltage Vfd_L (e.g., 1 V) generated at the resistance voltage dividing circuit in accordance with the drive signal φVRSEL received from the timing generation unit 25, and applies the voltage to all of the pixels and the dummy pixels 247 as the power supply voltage VR.

A reference voltage generation unit 246b illustrated in FIG. 5B includes: a resistance voltage dividing circuit including two resistances 291 and 292; and a switch (transistor) 294 driven by a drive signal φVSH. The reference voltage generation unit 246b generates clamp voltage Vclp of the noise removal unit 243 at the timing when the drive signal φVSH is driven by driving of the switch 294.

Known Method of Correcting Lateral Streak Noise

Figure 6A:
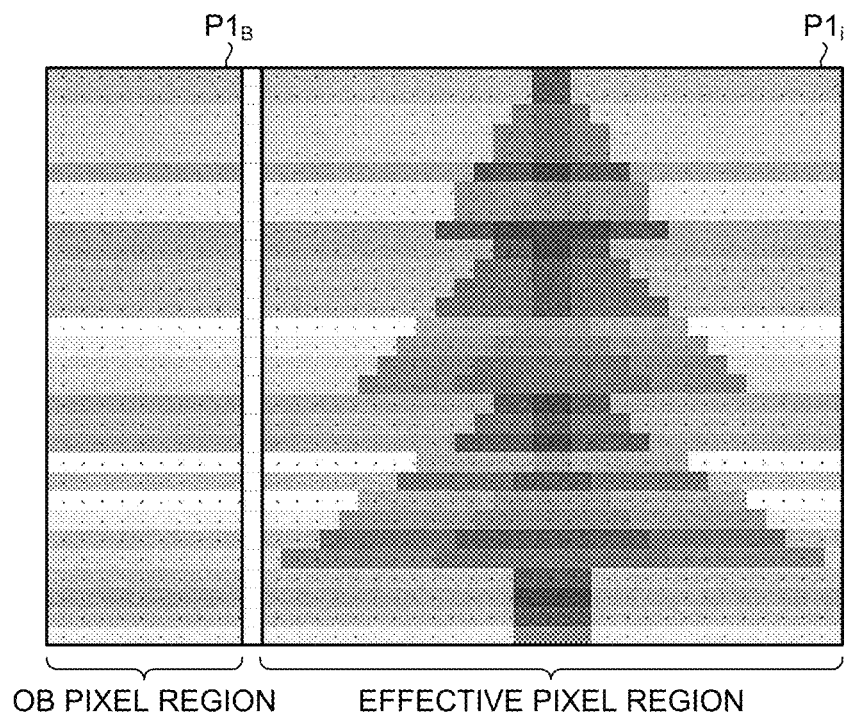
FIG. 6A is a view schematically illustrating an outline of a known method of correcting lateral streak noise.
Figure 6B:
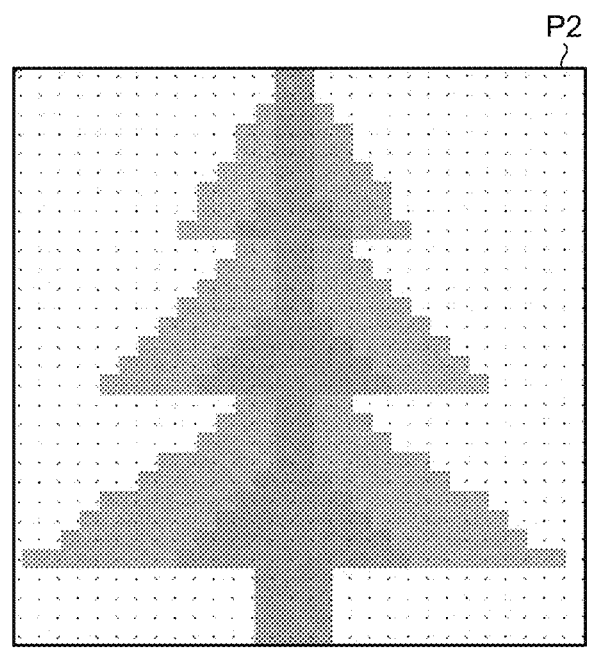
FIG. 6B is a view illustrating an exemplary image corrected by the known method of correcting lateral streak noise.
Figure 7A:
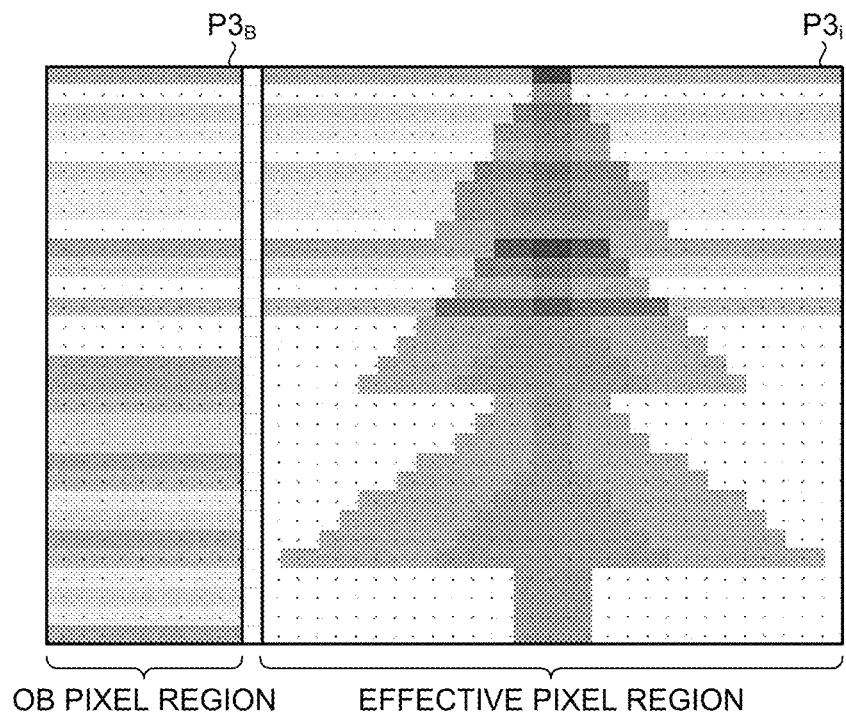
FIG. 7A is a view schematically illustrating a case where lateral streak noise may not be corrected by the known method of correcting lateral streak noise.
Figure 7B:
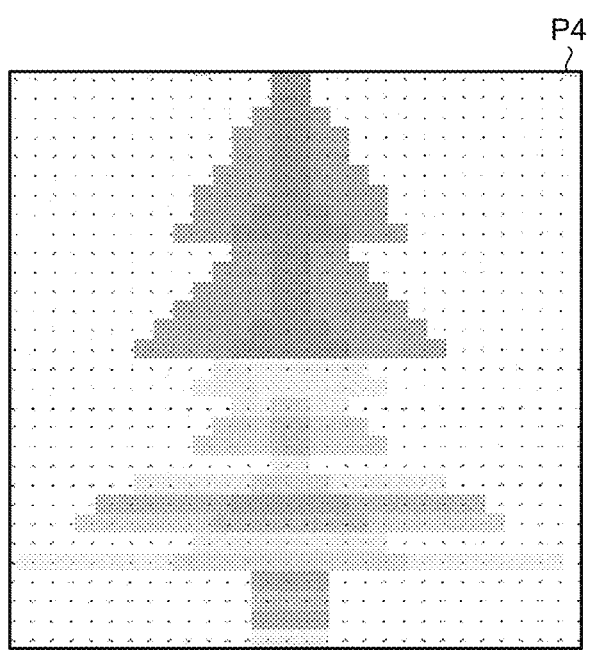
FIG. 7B is a view illustrating an exemplary image in a case where lateral streak noise may not be corrected by the known method of correcting lateral streak noise.

Next, a known method of correcting lateral streak noise will be described. FIG. 6A is a view schematically illustrating an outline of the known method of correcting lateral streak noise. FIG. 6B is a view illustrating an exemplary image corrected by the known method of correcting lateral streak noise. FIG. 7A is a view schematically illustrating a case where lateral streak noise may not be corrected by the known method of correcting lateral streak noise. FIG. 7B is a view illustrating an exemplary image in a case where lateral streak noise may not be corrected by the known method of correcting lateral streak noise. Note that, in FIG. 7A, it is assumed that lateral streak noise is uniformly generated in an entire portion of each row on an upper half of the image, and lateral streak noise is generated only in OB pixels in a lower half of the image.

As illustrated in FIG. 6A, in the known correction method, an average value of respective signal values of a plurality of OB pixels $P1_B$ in each horizontal line is defined as a clamp value, and this clamp value is subtracted from an imaging signal output from a pixel $P1_i$ of the same horizontal line in an effective pixel region not shielded from light. As a result, as illustrated in FIG. 6B, a high-quality pixel P2 having lateral streak noise corrected may be obtained.

On the other hand, as illustrated in FIG. 7A, in the known correction method, in a case where an average value of respective signal values of a plurality of OB pixels $P3_B$ in each horizontal line is defined as a clamp value and the clamp value is subtracted from an imaging signal output from a pixel $P3_i$ of the same horizontal line in the effective pixel region not shielded from light, a low-quality image P4 is obtained as illustrated in FIG. 7B because lateral streak noise may be normally corrected in the upper half while lateral streak noise is abnormally corrected in the lower half. A state that may possibly happen is that: rows illustrated in the upper half and rows illustrated in the lower half are generated randomly within one image as illustrated in FIG. 7A. Additionally, as for the state in the lower half, a case where lateral streak noise is generated only in the OB pixel region, a case where lateral streak noise is generated in a pixel in the effective pixel region, or a case where lateral streak noise is generated partly in pixels in the OB pixel region and the effective pixel region is deemed as the same state. In other words, in a case where the state illustrated in FIG. 7A occurs within one image (inside one frame), a high-quality image may not be obtained by adopting the known correction method. Therefore, in the first embodiment, the inspection device 6 calculates a clamp value for each first chip 21 (imaging element), and records the calculated clamp value in the connector recording unit 53 of the endoscope 2.

Outline of Lateral Streak Noise Correction Processing

Figure 8A:
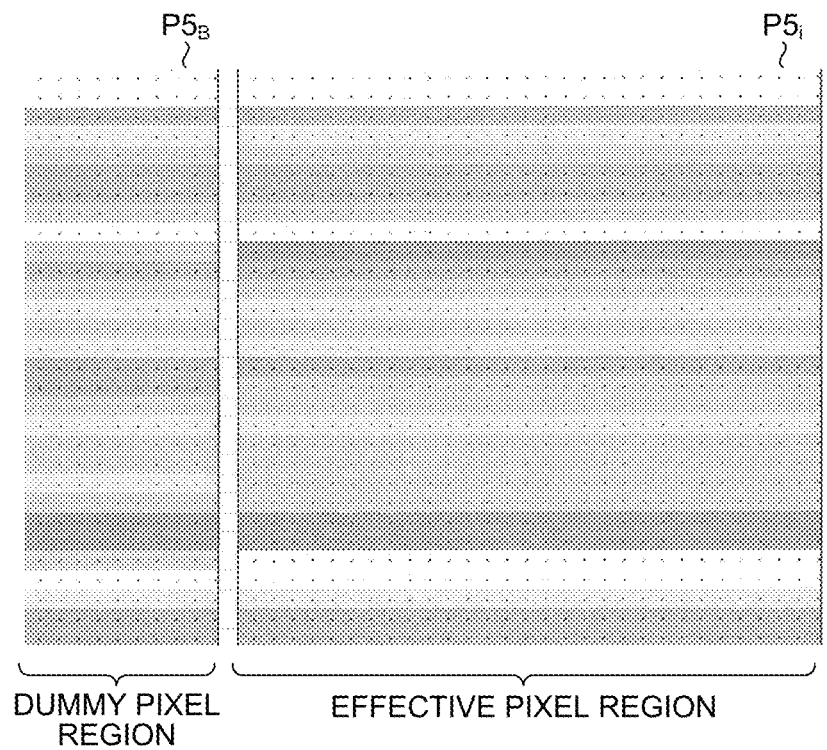
FIG. 8A is a view schematically illustrating a dark-time image corresponding to dark-time image data generated by an imaging unit according to the first embodiment.
Figure 8B:
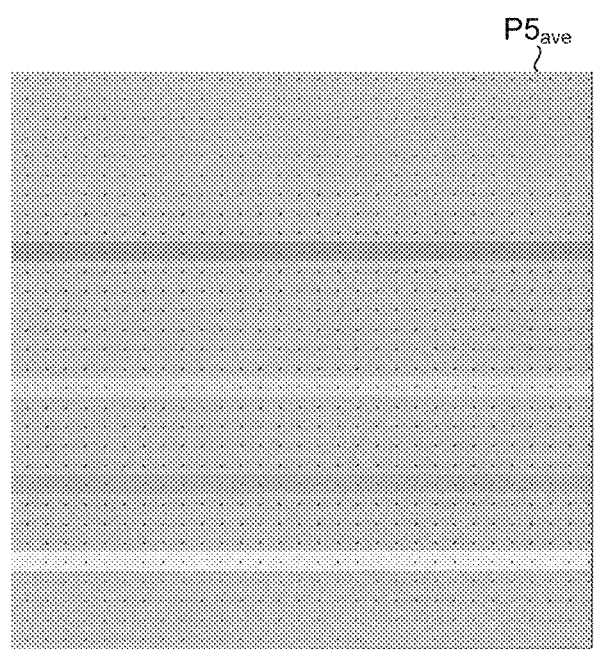
FIG. 8B is a view schematically illustrating a corrected image in which lateral streak noise included in dark-time image data is corrected according to the first embodiment.
Figure 8C:
FIG. 8C is a view schematically illustrating an average value of pixel values in each row of the imaging unit according to the first embodiment.

FIG. 8A is a view schematically illustrating a dark-time image corresponding to dark-time image data generated by the imaging unit 20. FIG. 8B is a view schematically illustrating a corrected image in which lateral streak noise included in dark-time image data is corrected. FIG. 8C is a view schematically illustrating an average value of pixel values in each row of the imaging unit 20.

As illustrated in FIG. 8A, in the first embodiment, the inspection device 6 calculates, based on dark-time image data generated by the imaging unit 20, a correction value (eigenvalue) including an optimal range of horizontal lines and a constant in order to correct lateral streak noise included in image data generated by the imaging unit 20. Specifically, in a case of calculating a clamp value from a pixel value of a dummy pixel $P5_B$, the inspection device 6 calculates a clamp value at the time of correcting a pixel value of an effective pixel $P5_i$ in each row by: vertically expanding a calculation range relative to a horizontal line to be corrected to increase the number of horizontal lines in the range; subtracting an average value of pixel values of dummy pixels $P5_B$ from a clamp value of each horizontal line; multiplying this subtraction calculation result by a coefficient (e.g., 0, 0.1, 0.2, . . . , 1.0); and adding the average value of the pixel values of the dummy pixels $P5_B$ again (processing 1).

After that, the inspection device 6 generates a corrected image $P5_{ave}$ (refer to FIG. 8B) in which lateral streak noise included in the image data of the effective pixel $P5_i$ is corrected by subtracting the clamp value of the corresponding horizontal line from a pixel value in each row of an effective pixels $P5_i$ in each row (processing 2).

Subsequently, the inspection device 6 calculates, as a lateral streak noise index, an average value $P5_{clp}$ (refer to FIG. 8C) of pixel values in each horizontal line (processing 3) for the corrected image $P5_{ave}$.

After that, the inspection device 6 calculates a plurality of lateral streak noise indices by sequentially performing the above-described processing 1 to 3 while changing a horizontal line to be corrected, a range of horizontal lines including a horizontal line to be corrected, and a coefficient, and then calculates a statistical value based on the plurality of calculated lateral streak noise indices, thereby calculating, as an eigenvalue (correction value), an optimal range of horizontal lines and an optimal coefficient in order to correct lateral streak noise included in image data generated by the imaging unit 20 (processing 4). For example, the inspection device 6 calculates a plurality of lateral streak noise indices by sequentially performing the above-described processing 1 to 3 while changing a horizontal line to be corrected, a range of horizontal lines including a horizontal line to be corrected, and a coefficient, and calculates a standard deviation of the plurality of calculated lateral streak noise indices, and then calculates, as a correction value (eigenvalue), a range of horizontal lines (number of rows) and a coefficient in which the standard deviation becomes minimum. Meanwhile, the inspection device 6 uses the standard deviation as a statistical value, but may also use any one of a weighted average value, a mode, a median value, a maximum value, and a minimum value, for example.

Processing of Inspection Device

Figure 9A:
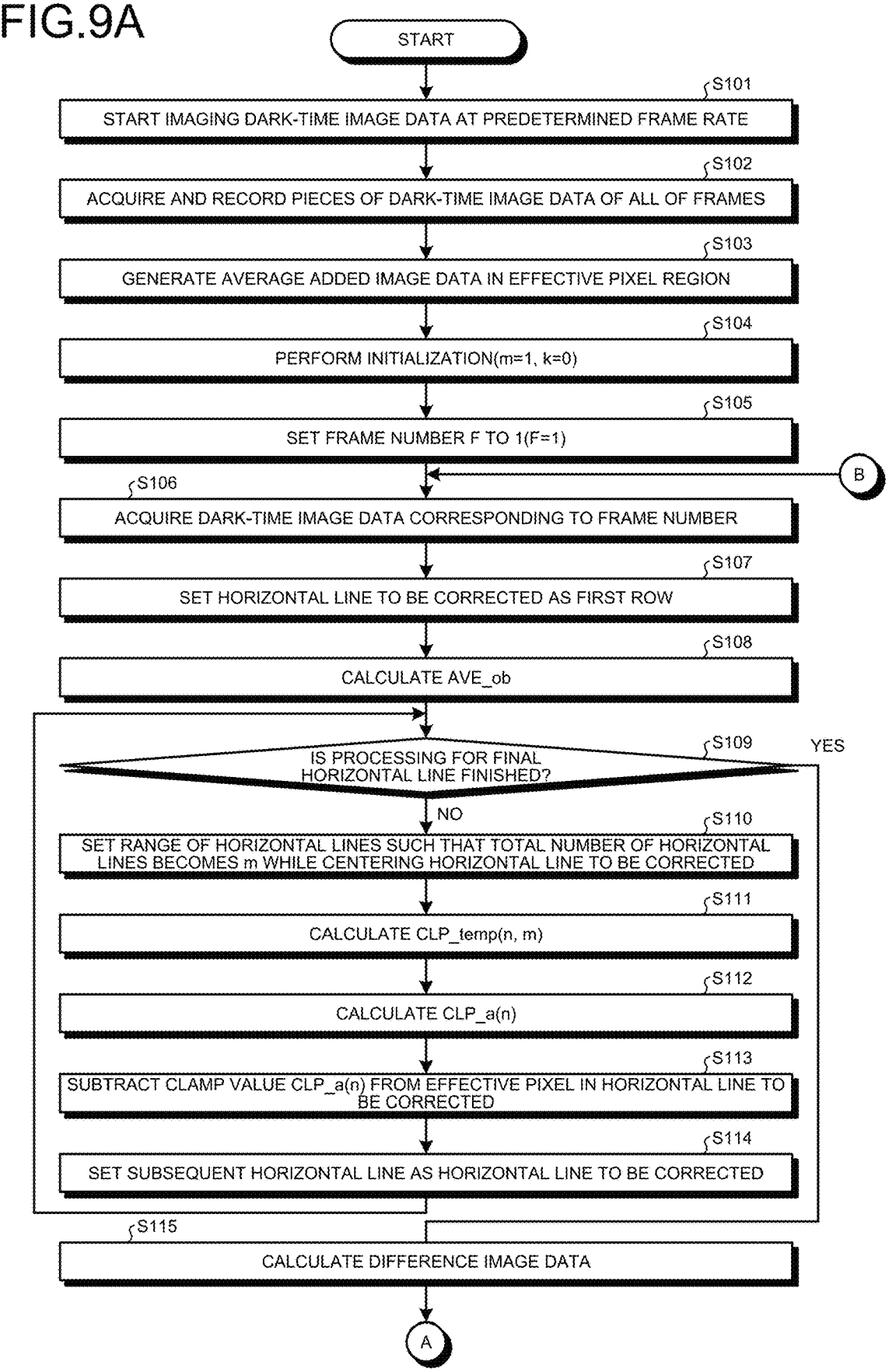
FIG. 9A is a flowchart illustrating an outline of processing executed by an inspection device to calculate an eigenvalue of an imaging unit according to the first embodiment.
Figure 9B:
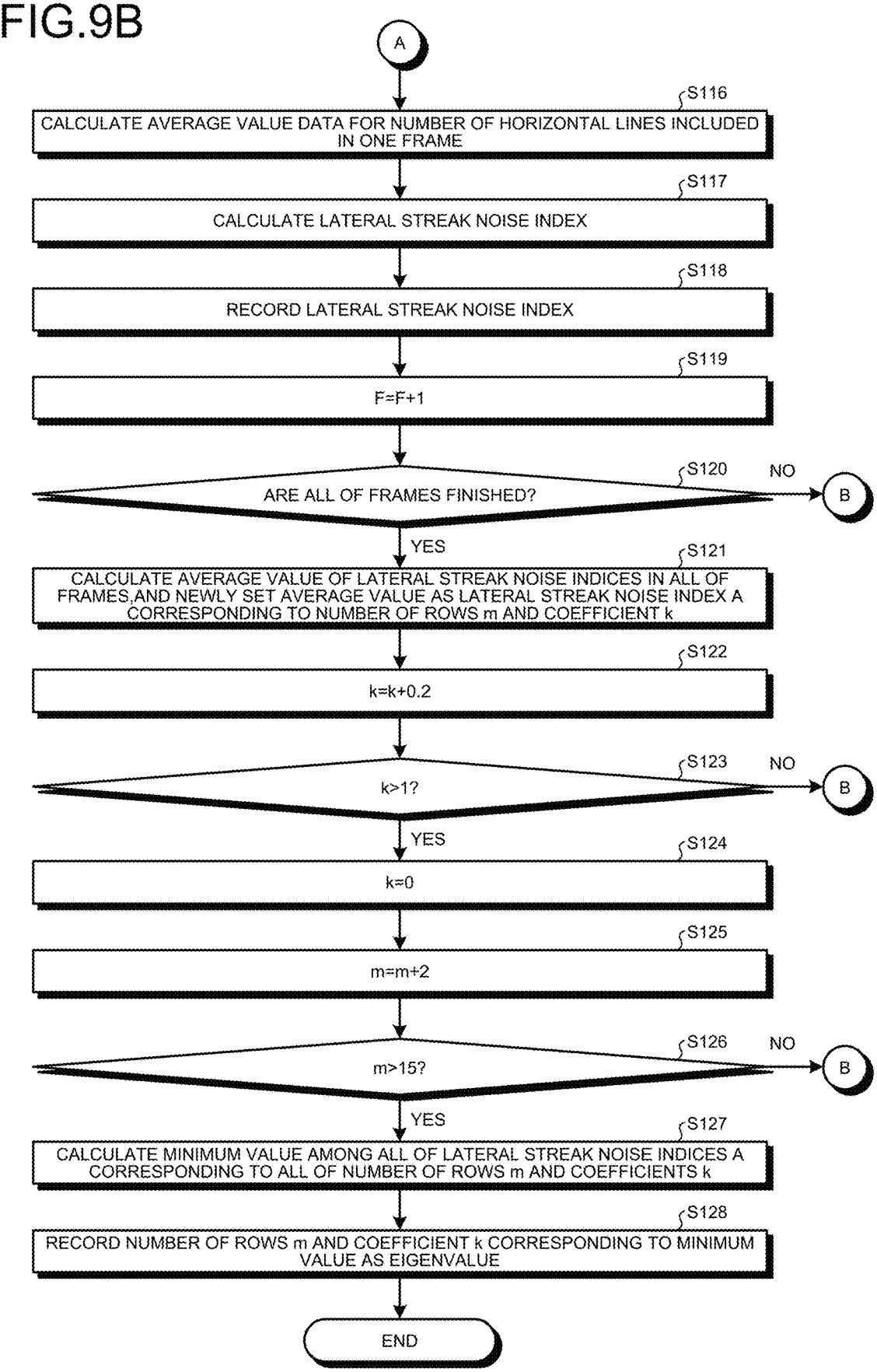
FIG. 9B is a flowchart illustrating the outline of processing executed by the inspection device to calculate an eigenvalue of an imaging unit according to the first embodiment.

Next, detailed processing executed by the inspection device 6 will be described. FIGS. 9A and 9B are flowcharts illustrating an outline of processing executed by the inspection device 6 to calculate an eigenvalue of the imaging unit 20.

As illustrated in FIG. 9A, the imaging control unit 650 first causes the endoscope 2 to start imaging dark-time image data at a predetermined frame rate (e.g., 30 fps) (step S101).

Subsequently, the acquisition unit 641 acquires, from the endoscope 2, pieces of dark-time image data of all of frames (e.g., 256 frames) generated by the imaging unit 20 of the endoscope 2, and records the acquired pieces of dark-time image data in the recording unit 63 (step S102).

After that, the first generation unit 642 acquires the pieces of dark-time image data of all of the frames recorded in the recording unit 63, adds up pixel values in an effective pixel region of the acquired pieces of dark-time image data of all of the frames, and then generates average added image data by dividing the added-up pixel value by the number of frames (step S103).

Subsequently, the image processing unit 64 initializes: a range m that indicating rows in the vertical direction including a target row in a dark image corresponding to the dark-time image data; and a coefficient k used in correcting lateral streak noise (m=1, k=0) (step S104), and sets a frame number F to 1 (F=1) (step S105).

After that, the image processing unit 64 acquires dark-time image data corresponding to a frame number from the recording unit 63 (step S106), and sets a horizontal line to be corrected as a first row (step S107).

Subsequently, the fifth calculation unit 643a extracts pixel values of dummy pixels of the dark-time image data acquired from the recording unit 63, and calculates an average value AVE_ob of the extracted pixel values of the dummy pixels (step S108). Specifically, as illustrated in FIG. 10, after extracting respective pixel values of all of dummy pixels in a range B1 of a dark-time image P10 acquired from the recording unit 63, the fifth calculation unit 643a calculates an average value AVE_ob by adding up the extracted pixel values of all of the respective dummy pixels and then dividing the added-up pixel value by the number of pixels of all of the dummy pixels.

Subsequently, in a case where clamp value calculation processing by the fourth calculation unit 643 is finished up to a final horizontal line (step S109: Yes), the inspection device 6 proceeds to step S115 described later. On the other hand, in a case where the clamp value calculation processing by the fourth calculation unit 643 is not finished up to the final horizontal line (step S109: No), the inspection device 6 proceeds to step S110 described later.

In step S110, the fourth calculation unit 643 sets a range B2 of horizontal lines such that the total number of horizontal lines becomes m while centering a horizontal line to be corrected.

Subsequently, after extracting pixel values of dummy pixels 247 in the range of horizontal lines (the number of rows) set in step S110 for the dark-time image data acquired from the recording unit 63, the sixth calculation unit 643b calculates a clamp value CLP_temp(n, m) by adding up the extracted pixel values of the dummy pixels 247 in the range of horizontal lines, and dividing the added-up pixel value by the number of pixels of the dummy pixels 247 in the range of horizontal lines (step S111). Specifically, as illustrated in FIG. 10, after extracting the pixel values of the dummy pixels 247 in the range m of horizontal lines m set in step S110 for the dark-time image P10 acquired from the recording unit 63, the sixth calculation unit 643b calculates the clamp value CLP_temp(n, m) by adding up the extracted pixel values of the dummy pixels 247 in the range m of horizontal lines, and dividing the added pixel value by the number of the dummy pixels 247 in the range m of horizontal lines. Note that n represents the number of horizontal lines (target rows) to be corrected.

After that, the seventh calculation unit 643c calculates a clamp value CLP_a(n) (step S112). Specifically, the seventh calculation unit 643c calculates the clamp value CLP_a(n) by Expression (1) below in a case where: a horizontal line to be corrected is defined as n, a range of horizontal lines is defined as m, an average value of dummy signals respectively output from one or a plurality of correction pixels in a dark-time image is defined as AVE_ob, an average value of dummy signals respectively output from one or a plurality of correction pixels in the range m of horizontal lines is defined as CLP_temp(n, m), and a coefficient indicating a correlation degree between a plurality of dummy pixels 247 and a plurality of unit pixels 230 in each horizontal line is defined as k.

$$CLP\_a(n) = (CLP\_temp(n,m) - AVE\_ob) \times k + AVE\_ob \quad (1)$$

Here, k satisfies $0 \leq k \leq 1$.

Subsequently, the clamp processing unit 644 subtracts, from a pixel value of a unit pixel 230 in a horizontal line to be corrected, the clamp value CLP_a(n) calculated by the seventh calculation unit 643*c* in step S112 (step S113). Specifically, as illustrated in FIG. 10, the clamp processing unit 644 applies, to a pixel value of a unit pixel 230 in a horizontal line A1 to be corrected, clamp processing to subtract the clamp value CLP_a(n) calculated by the seventh calculation unit 643*c*, and records a result of the clamp processing in the recording unit 63.

After that, the fourth calculation unit 643 sets a subsequent row as a horizontal line to be corrected (step S114), and the processing returns to the above-described step S109.

In step S115, the second generation unit 645 generates difference image data. Specifically, the second generation unit 645 generates the difference image data by subtracting, from dark-time image data corresponding to a frame number, the average added image data calculated by the first generation unit 642 in the above-described step S103.

Subsequently, the first calculation unit 646 calculates average value data in a range of horizontal lines within one frame (step S116). Specifically, the first calculation unit 646 calculates an average value in each horizontal line in the difference image data generated by the second generation unit 645 in step S115, and calculates average value data for horizontal lines (for number of rows) within one frame by dividing this calculation result by the number of horizontal lines (number of rows) of the difference image data. Meanwhile, the first calculation unit 646 calculates average value data in a range of horizontal lines within one frame, but not limited to thereto, may also calculate any one of a standard deviation, a median value, a mode, a weighted average value, a maximum value, and a minimum value, for example.

After that, the second calculation unit 647 calculates a lateral streak noise index (step S117). Specifically, the second calculation unit 647 calculates the lateral streak noise index based on the average value data in the range of horizontal lines calculated by the first calculation unit 646 in the above-described step S116. For example, the second calculation unit 647 calculates, as a lateral streak noise index of a current frame, any one of a standard deviation, a median value, a mode, a weighted average value, a maximum value, and a minimum value of the average value data in the range of horizontal lines calculated by the first calculation unit 646. Meanwhile, in the first embodiment, the second calculation unit 647 calculates, as a lateral streak noise index, a standard deviation of average value data in a range of horizontal lines calculated by the first calculation unit 646.

Subsequently, the second calculation unit 647 records, in the recording unit 63, the calculation result in step S117 (step S118).

After that, the image processing unit 64 increments the frame number (F=F+1) (step S119).

After that, in a case where all of the frames of the dark-time image data recorded in the recording unit 63 are finished (step S120: Yes), the inspection device 6 proceeds to step S121 described later. On the other hand, in a case where all of the frames of the dark-time image data recorded in the recording unit 63 are not finished (step S120: No), the inspection device 6 returns to the above-described step S106.

In step S121, the third calculation unit 648 calculates a lateral streak noise index A. Specifically, the third calculation unit 648 calculates the lateral streak noise index A based on lateral streak noise in all of frames. For example, the third calculation unit 648 calculates an average value of lateral streak noise indices in all of the frames and newly calculates the average value as a lateral streak noise index A(m, k) corresponding to a range m and a coefficient k.

Subsequently, the third calculation unit 648 adds 0.2 to the coefficient k (k=k+0.2) (step S122).

After that, in a case where the coefficient k exceeds 1 (k>1) (step S123: Yes), the inspection device 6 proceeds to step S124 described later. On the other hand, in a case where the coefficient k does not exceed 1 (step S123: No), the inspection device 6 returns to the above-described step S106.

In step S124, the third calculation unit 648 initializes the coefficient k (k=0).

Subsequently, the third calculation unit 648 adds 2 to the range m (m=m+2) (step S125). Note that a value to be added to the range m may be suitably changed, and may also be 1, 3, or the like, for example.

After that, in a case where the range m exceeds 15 (m>15) (step S126: Yes), the inspection device 6 proceeds to step S127 described later. On the other hand, in a case where the range m does not exceed 15 (step S126: No), the inspection device 6 returns to step S106.

In step S127, the third calculation unit 648 calculates a minimum value among all of the lateral streak noise indices A corresponding to all of ranges m and coefficients k recorded in the recording unit 63.

Subsequently, the recording control unit 649 records, as an eigenvalue (correction value) of the imaging unit 20, a range m of horizontal lines including a horizontal line to be corrected and a coefficient k in the eigenvalue information recording unit 531 of the connector recording unit 53 of the endoscope 2, and here, the range m and coefficient k correspond to the lateral streak noise index having the minimum value calculated by the third calculation unit 648 (step S128). After step S128, the inspection device 6 finishes the present processing.

Thus, the inspection device 6 calculates a correction value of the imaging unit 20 used in correcting lateral streak noise included in image data generated by the imaging unit 20, and records the calculation result in the eigenvalue information recording unit 531 of the connector recording unit 53 of the endoscope 2.

Configuration of Endoscope System

Figure 11:
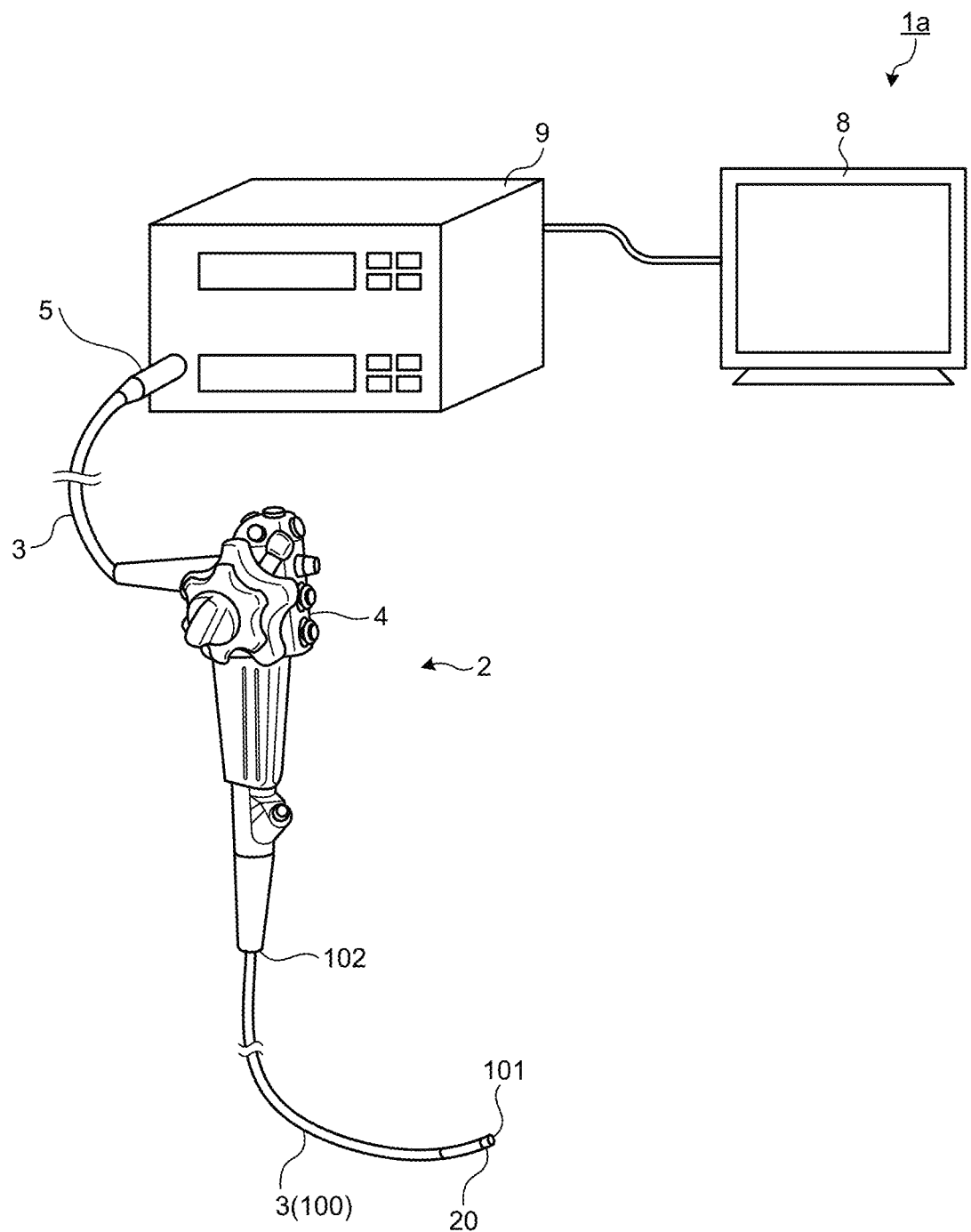
FIG. 11 is a perspective view illustrating an entire structure of an endoscope system according to the first embodiment.
Figure 12:
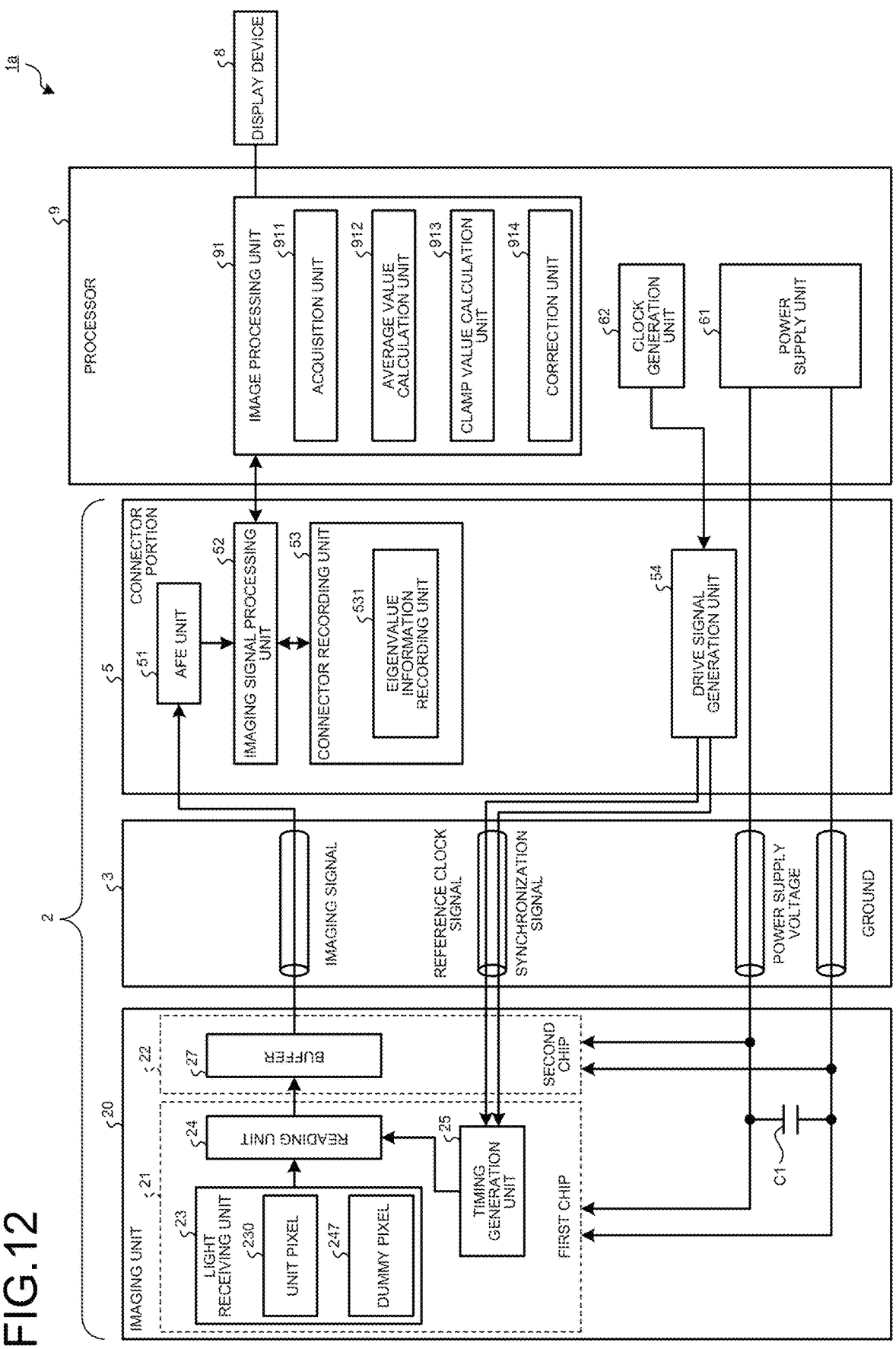
FIG. 12 is a block diagram illustrating a functional configuration of the endoscope system according to the first embodiment.

Next, an endoscope system including the above-described endoscope 2 will be described. FIG. 11 is a view schematically illustrating an entire structure of the endoscope system. FIG. 12 is a block diagram schematically illustrating a configuration of the endoscope system.

An endoscope system 1*a* illustrated in FIGS. 11 and 12 includes an endoscope 2 described above, a display device 8, and a processor 9 (image processing device).

The display device 8 displays an image for an image signal applied with image processing by the processor 9. Additionally, the display device 8 displays various kinds of information related to the endoscope system 1*a*. The display device 8 is formed by using a display panel or the like, such as a liquid crystal or an organic electro luminescence (EL).

The processor 9 integrally controls the entire endoscope system 1*a*, is formed by using, for example, a halogen lamp, a white light emitting diode (LED), or the like, and emits illumination light to a subject from a distal end side of the inserting portion 100 of the endoscope 2 via the connector portion 5 and the transmission cable 3. The processor 9 includes a power supply unit 61, a clock generation unit 62, and an image processing unit 91. Note that a description of an illumination mechanism inside the processor 9 will be omitted.

The image processing unit 91 applies, to a digital imaging signal subjected to signal processing by the imaging signal processing unit 52, image processing such as synchronization processing, white balance (WB) adjustment processing, gain adjustment processing, gamma correction processing, digital analog (D/A) conversion processing, and format conversion processing, and converts the signal into an image signal, and then outputs the image signal to the display device 8. The image processing unit 91 includes an acquisition unit 911, an average value calculation unit 912, a clamp value calculation unit 913, and a correction unit 914.

The acquisition unit 911 acquires, from the connector recording unit 53 of the connector portion 5 of the endoscope 2 connected to the processor 9: eigenvalue information that includes a correction value to correct lateral streak noise and relates to parameters needed to apply image processing to image data generated by the imaging unit 20; and the image data generated by the imaging unit 20, respectively. Here, the correction value includes: a range m of horizontal lines (number of rows) including a horizontal line to be corrected, and located in the vertical direction while setting the horizontal line as a reference; and a coefficient k indicating a correlation degree between a plurality of dummy pixels 247 and a plurality of unit pixels 230 in each horizontal line.

The average value calculation unit 912 calculates an average value of dummy signals respectively output from the plurality of dummy pixels 247 in the image corresponding to the image data acquired by the acquisition unit 911.

The clamp value calculation unit 913 calculates, for each horizontal line, a clamp value in order to correct an imaging signal of each of the plurality of unit pixels 230 based on: the average value of dummy signals calculated by the average value calculation unit 912 and respectively output from the plurality of dummy pixels 247; and the range m of horizontal lines and coefficient k of the correction value acquired by the acquisition unit 911.

The correction unit 914 corrects an imaging signal of each of the plurality of unit pixels 230 in the horizontal line to be corrected based on the clamp value calculated by the clamp value calculation unit 913 for each horizontal line.

Processing by Processor

Figure 13:
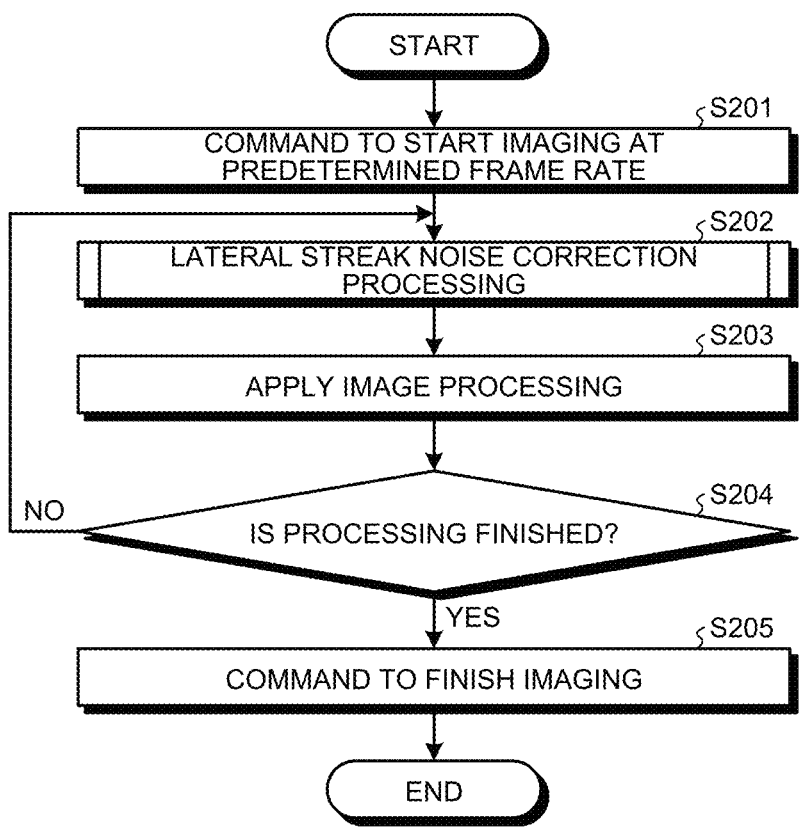
FIG. 13 is a flowchart illustrating an outline of processing executed by a processor according to the first embodiment.

Next, processing of the processor 9 will be described. FIG. 13 is a flowchart illustrating an outline of the processing executed by the processor 9.

As illustrated in FIG. 13, the processor 9 first commands the connected endoscope 2 to start imaging at a predetermined frame rate (step S201). In this case, the processor 9 causes a light source unit (not illustrated) to emit illumination light to the endoscope 2.

Subsequently, the image processing unit 91 executes lateral streak noise correction processing to correct lateral streak noise included in image data generated by the endoscope 2 (step S202). Note that details of the lateral streak noise correction processing will be described later.

After that, the image processing unit 91 applies predetermined image processing to the image data having lateral streak noise corrected, and outputs the same to the display device 8 (step S203). For example, the image processing unit 91 applies, to the image data having the lateral streak noise corrected, addition processing to add an offset value of the imaging unit 20, WB adjustment processing to adjust white balance, gain adjustment processing to adjust gain, and the like, and outputs the image data to the display device 8.

Subsequently, in a case where a command signal to finish observation on a subject is received from the operating unit 4 (step S204: Yes), the processor 9 commands the endoscope 2 to finish imaging (step S205) and finishes the present processing.

In step S204, in a case where the command signal to finish observation on the subject is not received from the operating unit 4 (step S204: No), the processor 9 returns to step S202.

Lateral Streak Noise Correction Processing

Figure 14:
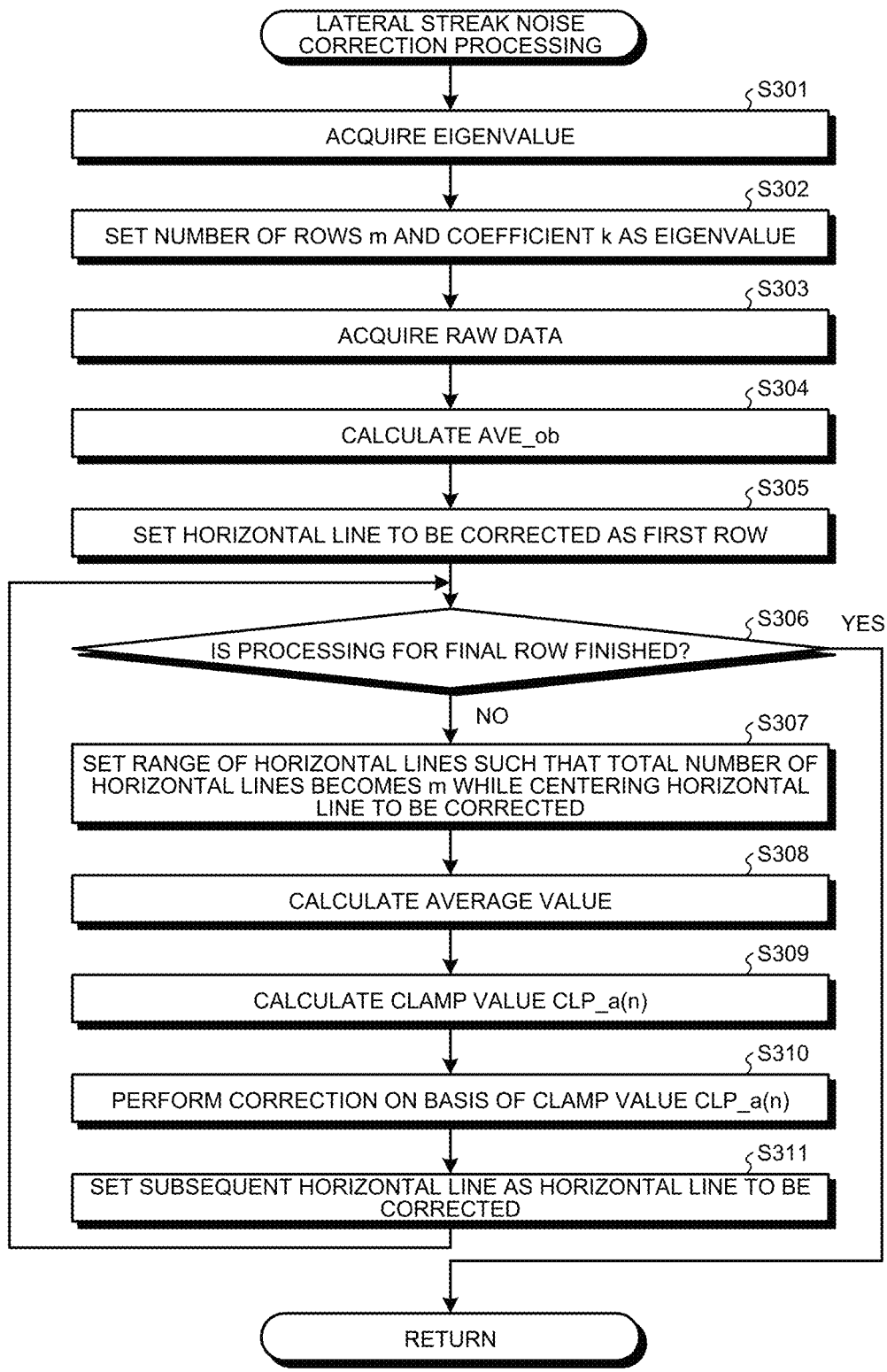
FIG. 14 is a flowchart illustrating an outline of lateral streak noise correction processing in FIG. 13.

Next, an outline of the lateral streak noise correction processing described in step S202 of FIG. 13 will be described. FIG. 14 is a flowchart illustrating the outline of the lateral streak noise correction processing in FIG. 13.

As illustrated in FIG. 14, the acquisition unit 911 first acquires an eigenvalue from the eigenvalue information recording unit 531 of the connector recording unit 53 in the endoscope 2 (step S301), and sets a range m of a horizontal line to be corrected and a coefficient k as the eigenvalue (correction value) (step S302).

Subsequently, the average value calculation unit 912 acquires RAW data generated by the endoscope 2 (step S303), calculates an average value AVE_ob based on pixel values of dummy pixels included in the acquired RAW data (step S304), and sets the horizontal line to be corrected as a first row (step S305). Specifically, the average value calculation unit 912 adds up the pixel values of the dummy pixels included in the RAW data, and calculates the average value AVE_ob by dividing the added-up result by the number of pixels of the dummy pixels.

After that, in a case where the horizontal line to be corrected is a final horizontal line of the imaging unit 20 (step S306: Yes), the processor 9 returns to a main routine in FIG. 13. On the other hand, in a case where the horizontal line to be corrected is not the final horizontal line of the imaging unit 20 (step S306: No), the processor 9 proceeds to step S307.

In step S307, the clamp value calculation unit 913 sets a range of horizontal lines (range of rows) such that a total range of horizontal lines becomes m while centering a horizontal line to be corrected. In this case, when a row number of a horizontal line in an effective pixel region of the imaging unit 20 is a first row, the range of horizontal lines is set such that the total number of the horizontal lines becomes m, including a row in a light shielding region. For example, in a case where the range m is 3, when the row number of the horizontal lines to be corrected in the effective pixel region of the imaging unit 20 is the first row (first horizontal line), the image processing unit 91 sets, as the range of horizontal lines to be corrected, a horizontal line located on a previous stage (upper side) of the horizontal line to be corrected or a horizontal line used to obtain a reference signal and a horizontal line located on a subsequent stage (lower side) of the horizontal line to be corrected.

Subsequently, the clamp value calculation unit 913 calculates an average value of pixel values of dummy pixels in the range of horizontal lines set in step S307 based on the pixel values of the dummy pixels in the range of horizontal lines set in step S307 (Step S308). Specifically, the clamp value calculation unit 913 calculates the average value of the pixel values of the dummy pixels in the range of horizontal lines set in step S307 by adding up all of the pixel values of the dummy pixels in the range of horizontal lines set in step S307 and then dividing the added-up result by the number of pixels of the dummy pixels.

After that, the clamp value calculation unit 913 calculates a clamp value CLP_a (step S309). Specifically, the clamp value calculation unit 913 calculates the clamp value CLP_a by using Expression (1) described above, the average value calculated in step S308 described above, the coefficient k, and the average value AVE_ob calculated in step S304 described above.

Subsequently, the correction unit 914 corrects, based on the clamp value calculated in step S309, pixel values of unit pixels 230 in the horizontal line to be corrected (step S310). Specifically, the correction unit 914 corrects image data in an effective pixel region in the horizontal line to be corrected by subtracting the clamp value CLP_a from a pixel value output from each of the unit pixels 230 in the effective pixel region in the horizontal line to be corrected.

After that, the image processing unit 91 sets a subsequent row as a horizontal line to be corrected (step S311). After step S311, the processor 9 returns to the above-described step S306.

According to the first embodiment described above, the first calculation unit 646 calculates, as a lateral streak noise index, a statistical value of difference image data for each frame generated by the second generation unit 645, the second calculation unit 647 calculates, for each of correlation degrees between a plurality of dummy pixels 247 and a plurality of unit pixels 230 in each horizontal line, a plurality of lateral streak noise indices calculated by the first calculation unit 646 for each frame, the third calculation unit 648 calculates, as a correction value to correct lateral streak noise included in image data, a correlation degree having a minimum value among the plurality of lateral streak noise indices calculated by the second calculation unit 647 for each of correlation degrees, and the recording control unit 649 records the correction value calculated by the third calculation unit 648 in the eigenvalue information recording unit 531 of the connector recording unit 53 in the endoscope 2. Therefore, the lateral streak noise may be corrected with high accuracy in each first chip 21 even in a case where kinds of noise different from each other are generated in an OB pixel region and an effective pixel region due to fluctuation in power supply voltage.

Additionally, according to the first embodiment, since dummy pixel 247 that generates a dummy signal equivalent to an OB pixel shielded from light is used, lateral streak noise may be corrected with high accuracy in each first chip 21 even in a case where an OB pixel needed to calculate a clamp value may not be arranged in a first chip 21, and therefore, the area of the first chip 21 may be reduced. Meanwhile, in the first embodiment, the example in which a dummy pixel 247 that is equivalent to an OB pixel and generates a dummy signal has been described as an example of a correction pixel that outputs a dummy signal, but an OB pixel shielded from light is also applicable.

Furthermore, according to the first embodiment, the average value calculation unit 912 calculates an average value of dummy signals respectively output from a plurality of dummy pixels 247 in an image corresponding to image data acquired by the acquisition unit, the clamp value calculation unit 913 calculates, for each horizontal line, a clamp value to correct respective imaging signals of a plurality of unit pixels 230 based on the average value of the dummy signals respectively output from the plurality of dummy pixels 247 calculated by the average value calculation unit 912, a range of horizontal lines in the imaging unit 20, and a coefficient, and the correction unit 914 corrects respective imaging signals of the plurality of unit pixels 230 in a horizontal line to be corrected based on the clamp value calculated by the clamp value calculation unit 913 for each horizontal line. Therefore, even in a case where kinds of noise different from each other are generated in an OB pixel portion and an effective pixel portion respectively due to fluctuation in power supply voltage, lateral streak noise may be corrected with high accuracy in each first chip 21.

Second Embodiment

Next, a second embodiment will be described. The second embodiment has a configuration similar to that of a first embodiment described above, and processing executed by an inspection device and lateral streak noise correction processing executed by a processor are different. In the following, processing executed by each of the inspection device and the processor according to the second embodiment will be described. Note that components same as those of an inspection system 1 and the endoscope system 1a according to the above-described first embodiment will be denoted by the same reference signs, and a description thereof will be omitted.

Processing of Inspection Device

Figure 15A:
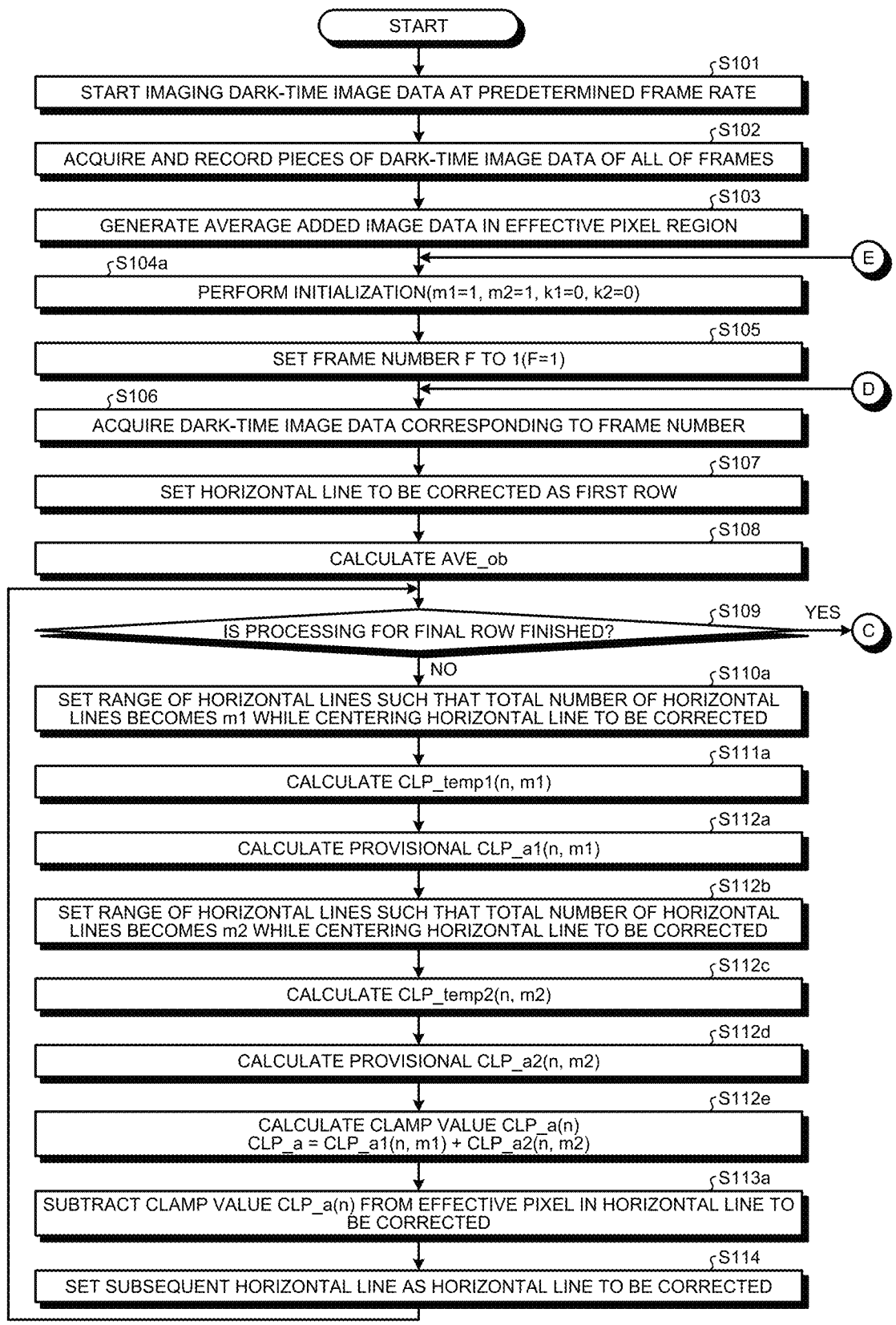
FIG. 15A is a flowchart illustrating an outline of processing executed by an inspection device to calculate an eigenvalue of an imaging unit according to a second embodiment.
Figure 15B:
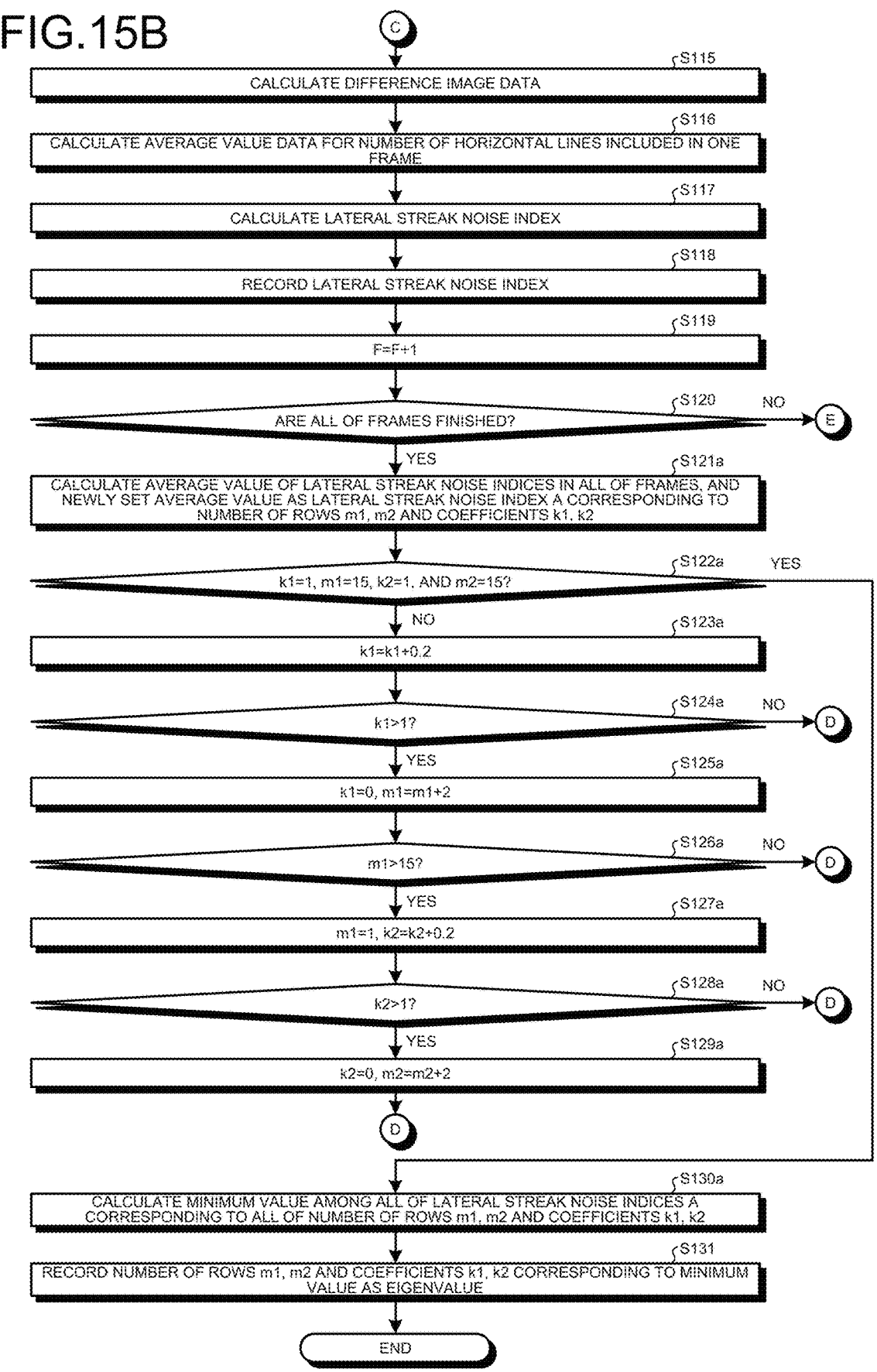
FIG. 15B is a flowchart illustrating the outline of processing executed by the inspection device to calculate an eigenvalue of the imaging unit according to the second embodiment.
Figure 16:
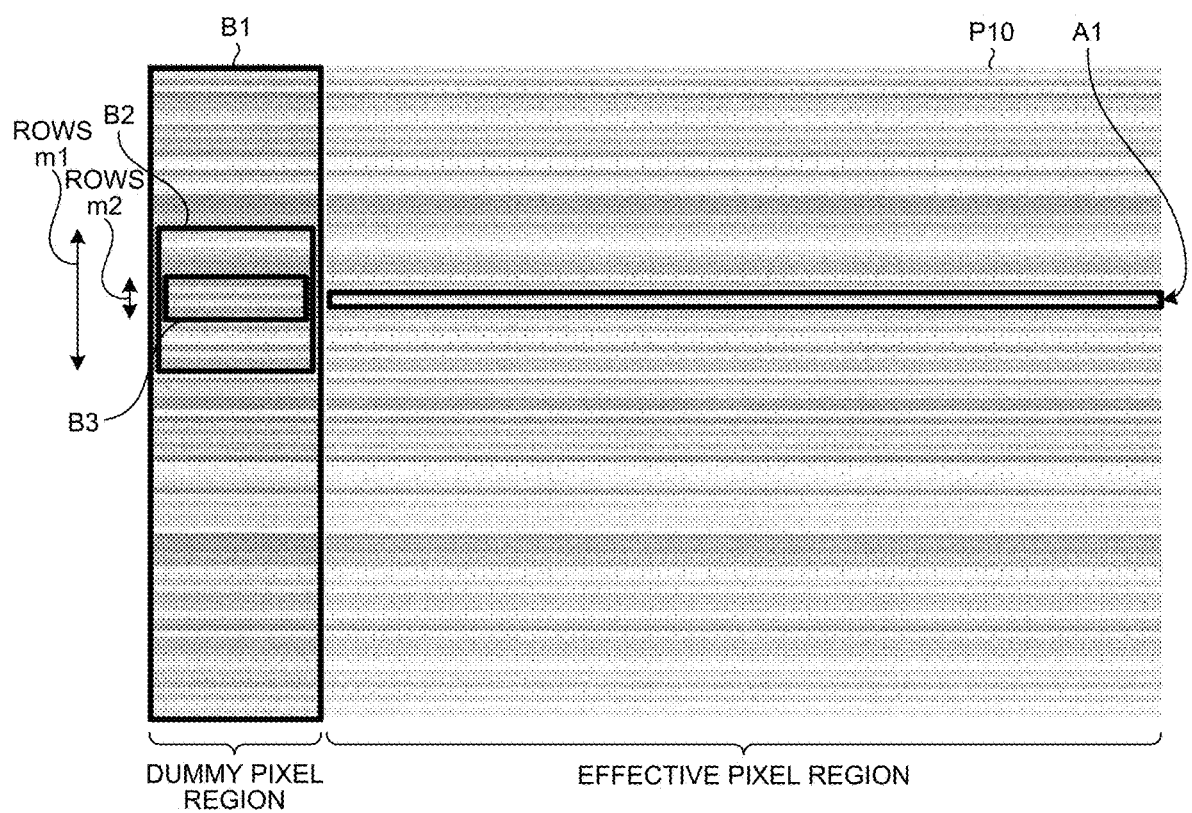
FIG. 16 is a view schematically illustrating a calculating method executed by the inspection device to calculate an eigenvalue of an imaging unit according to the second embodiment.

First, processing executed by an inspection device 6 according to the second embodiment will be described. FIG. 15A and FIG. 15B are flowcharts illustrating an outline of processing executed by the inspection device 6 to calculate an eigenvalue of an imaging unit 20 according to the second embodiment. FIG. 16 is a view schematically illustrating a calculating method executed by the inspection device 6 to calculate an eigenvalue of the imaging unit 20 according to the second embodiment. In FIG. 15A and FIG. 15B, the inspection device 6 executes steps S104a, S110a, S111a, S112a, S113a, and S121a to S130a in the second embodiment instead of steps S104, S110, S111, S112, S113, and S121 to S127 of FIG. 9 in the above-described first embodiment. Additionally, steps S112b to S112e are executed in FIG. 15A. Since other processing is similar to that of FIG. 9, a description thereof will be omitted.

In step S104a, an image processing unit 64 performs initialization as next (m1=1, m2=1, k1=0, k2=0) in which m1 represents a range of rows that include a target row in a dark-time image corresponding to dark-time image data and are located in a vertical direction, m2 represents a range of rows that are different from those of the range m1, include the target row in the dark-time image corresponding to the dark-time image data, and are located in the vertical direction, and k1, k2 are coefficients used at time of correcting lateral streak noise.

In step S110a, a fourth calculation unit 643 sets the range m1 of horizontal lines such that the total number of horizontal lines becomes m1 while centering a horizontal line to be corrected.

Subsequently, a sixth calculation unit 643b extracts pixel values of dummy pixels 247 in the range of horizontal lines set in step S110a from dark-time image data acquired from a recording unit 63, then adds up the extracted pixel values of the dummy pixels 247 in the range of rows, and calculates a clamp value CLP_temp1(n, m1) by dividing the added-up pixel values by the number of the dummy pixels 247 included in the range of horizontal lines (step S111a). As illustrated in FIG. 16, after extracting pixel values of dummy pixels 247 in a range B1 of a dark-time image P10 corresponding to the range m1 of horizontal lines, the sixth calculation unit 643b adds up the extracted pixel values of the dummy pixels 247 in the range of horizontal lines, and calculates the clamp value CLP_temp1(n, m1) by dividing the added-up pixel value by the number of the dummy pixels 247 in the range m1 of horizontal lines.

After that, a seventh calculation unit 643c calculates a provisional clamp value CLP_a1(n, m1) (step S112a). Specifically, the seventh calculation unit 643c calculates the provisional clamp value CLP_a1(n, m1) by Expression (2) below.

$$CLP\_a1(n,m1)=(CLP\text{temp}1(n,m1)-\text{AVE}\_ob)\times k1+(\text{AVE}\_ob+2) \quad (2)$$

Here, k1 satisfies 0≤k1≤1.

Subsequently, the fourth calculation unit 643 sets a range m2 of horizontal lines such that the total number of horizontal lines becomes m2 while centering the horizontal line to be corrected (step S112b).

After that, the sixth calculation unit 643b extracts pixel values of dummy pixels 247 in the range of horizontal lines set in step S110a from dark-time image acquired from the recording unit 63, then adds up the extracted pixel values of the dummy pixels 247 in the range of rows, and calculates a clamp value CLP_temp2(n, m2) by dividing the added-up pixel value by the number of pixels of the dummy pixels 247 in the range of horizontal lines (step S112c). Specifically, as illustrated in FIG. 16, the sixth calculation unit 643b extracts pixel values of dummy pixels 247 in a range B3 of the dark-time image P10 corresponding to the range m2 of horizontal lines, then adds up the extracted pixel values of the dummy pixels 247 in the range of rows, and calculates the clamp value CLP_temp2(n, m2) by dividing the added-up pixel value by the number of dummy pixels 247 in the range m2 of horizontal lines.

Subsequently, the seventh calculation unit 643c calculates a provisional clamp value CLP_a2(n, m2) (step S112d). Specifically, the seventh calculation unit 643c calculates the provisional clamp value CLP_a2(n) by Expression (3) below.

$$CLP\_a2(n,m2)=(CLP\_\text{temp}2(n,m2)-\text{AVE}\_ob)\times k2+(\text{AVE}\_ob+2) \quad (3)$$

Here, k2 satisfies 0≤k2≤1.

After that, the seventh calculation unit 643c calculates a clamp value CLP_a(n) (step S112e). Specifically, the seventh calculation unit 643c calculates the clamp value CLP_a(n) by using the provisional clamps calculated in the respective steps S112a and S112d. More specifically, the seventh calculation unit 643c calculates the clamp value CLP_a(n) by Expression (4) below.

$$CLP\_a(n)=CLP\_a1(n,m1)+CLP\_a2(n,m2) \quad (4)$$

Subsequently, the clamp processing unit 644 subtracts the clamp value CLP_a(n) calculated by the seventh calculation unit 643c in step S112e from a unit pixel 230 in the horizontal line to be corrected (step S113a). Specifically, as illustrated in FIG. 16, the clamp processing unit 644 subtracts the clamp value CLP_a(n) from a pixel value of a unit pixel 230 in a horizontal line A1 to be corrected, and records a result in the recording unit 63.

In step S121a, a third calculation unit 648 calculates a lateral streak noise index A. Specifically, the third calculation unit 648 calculates the lateral streak noise index A based on lateral streak noise in all of frames. For example, the third calculation unit 648 calculates an average value of lateral streak noise of all of frames, and newly calculates the same as lateral streak noise indices A (m1, m2, k1, k2) corresponding to the ranges m1, m2 and the coefficients k1, k2.

Subsequently, in a case where the coefficient k1 is 1 (k1=1), the coefficient k2 is 1 (k2=1), the range m1 is 15 (m1=15), and the range m2 is 15 (m2=15) (step S122a: Yes), the inspection device 6 suspends calculation and recording of the lateral streak noise indices, and proceeds to step S130a. On the other hand, in a case where any one of the conditions is not satisfied (step S122a: No), the inspection device 6 proceeds to step S123a described later.

The third calculation unit 648 adds 0.2 to the coefficient k1 (k1=k1+0.2) (step S123a). As a result, in a case where k1 exceeds 1 (k1>1) (step S124a: Yes), the inspection device 6 proceeds to step S125a described later. On the other hand, in a case where k1 does not exceed 1 (step S123a: No), the inspection device 6 proceeds to the above-described step S106.

In step S125a, the third calculation unit 648 adds 2 to the range m1 (m1=m1+2) while setting the coefficient k1 to 0 (k1=0).

Subsequently, in a case where m1 exceeds 15 (m1>15) (step S126a: Yes), the inspection device 6 proceeds to step S127a described later. On the other hand, in a case where m1 does not exceed 15 (step S126a: No), the inspection device 6 proceeds to step S106 described above.

In step S127a, the third calculation unit 648 adds 0.2 to the coefficient k2 (k2=k2+0.2) while setting the range m1 to 1 (m1=1).

Subsequently, in a case where k2 exceeds 1 (k2>1) (step S128a: Yes), the inspection device 6 proceeds to step S129a described later. On the other hand, in a case where k2 does not exceed 1 (step S128a: No), the inspection device 6 proceeds to the above-described step S106.

In step S129a, the third calculation unit 648 adds 2 to the range m2 (m2=m2+2) while setting the coefficient k2 to 0 (k2=0). After step S129a, the inspection device 6 proceeds to step S106 described above. Meanwhile, a value to be added to the above-mentioned ranges m1, m2 may be suitably changed, and may be 1, 3, or the like, for example.

In step S130a, the third calculation unit 648 calculates a minimum value among all of the lateral streak noise indices A corresponding to all of the ranges m1, m2 and the coefficients k1, k2 recorded in the recording unit 63.

Subsequently, the recording control unit 649 records, as eigenvalues (correction values) of the imaging unit 20, the ranges m1, m2 of horizontal lines including a horizontal line to be corrected and the coefficients k1, k2 in an eigenvalue information recording unit 531 of a connector recording unit 53 of the endoscope 2, in which the ranges m1, m2 and the coefficients k1, k2 correspond to the minimum value calculated by the third calculation unit 648 (step S131). After step S131, the inspection device 6 is finishes the present processing.

Thus, the inspection device 6 calculates a correction value to correct lateral streak noise included in image data generated by the imaging unit 20, and records the same in the eigenvalue information recording unit 531 of the connector recording unit 53 of the endoscope 2.

Lateral Streak Noise Correction Processing

Figure 17:
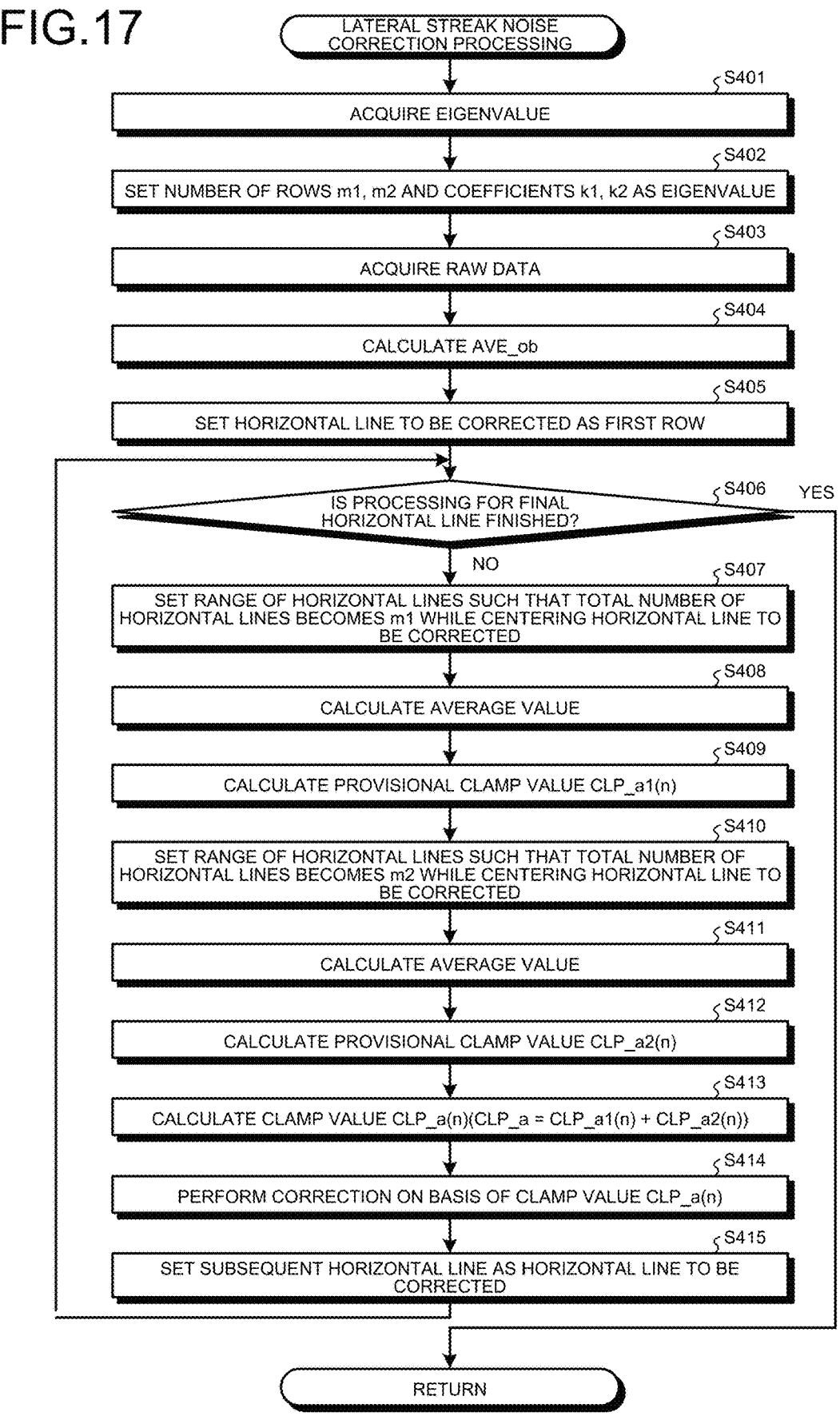
FIG. 17 is a flowchart illustrating an outline of lateral streak noise correction processing executed by a processor according to the second embodiment.

Next, lateral streak noise correction processing executed by a processor 9 will be described. FIG. 17 is a flowchart illustrating an outline of the lateral streak noise correction processing executed by the processor 9. Steps S401 to S406 correspond to steps S301 to S306 described above in FIG. 14, respectively.

In step S407, an image processing unit 91 sets a range of horizontal lines (number of rows) such that a total range of horizontal lines becomes m1 while centering a horizontal line to be corrected.

Subsequently, an average value calculation unit 912 calculates an average value of pixel values of dummy pixels in a range of horizontal lines based on pixel values of dummy pixels in the range of horizontal lines set in step S407 (step S408). Specifically, the average value calculation unit 912 calculates an average value of the pixel values of the dummy pixels in the range of horizontal lines by adding up all of the pixel values of the dummy pixels in the range of horizontal lines and then dividing the added-up result by the number of pixels of the dummy pixels.

After that, a clamp value calculation unit 913 calculates a provisional clamp value CLP_a1 (step S409). Specifically, the clamp value calculation unit 913 calculates the provisional clamp value CLP_a1 by using Expression (2) described above, the average value calculated by the average value calculation unit 912 in step S408 described above, a coefficient k1, and an average value AVE_ob calculated in step S404.

Subsequently, the image processing unit 91 sets a range of horizontal lines such that total number of horizontal lines becomes m2 while centering horizontal line to be corrected (step S410).

After that, the average value calculation unit 912 calculates an average value of pixel values of dummy pixels in the range of horizontal lines based on the pixel values of the dummy pixels in the range of horizontal lines set in step S410 (step S411). Specifically, the average value calculation unit 912 calculates an average value of the pixel values of the dummy pixels in the range of horizontal lines by adding up all of the pixel values of the dummy pixels in the range of horizontal lines and then dividing the added-up result by the number of pixels of the dummy pixels.

Subsequently, the clamp value calculation unit 913 calculates a provisional clamp value CLP_a2 (step S412). Specifically, the clamp value calculation unit 913 calculates the provisional clamp value CLP_a2 by using Expression (3) described above, the average value calculated in step S411 described above, a coefficient k2, and the average value AVE_ob calculated in the step S404.

After that, the clamp value calculation unit 913 calculates a clamp value CLP_a (step S413). Specifically, the clamp value calculation unit 913 calculates the clamp value CLP_a by adding the provisional clamp value CLP_a1 calculated in step S409 to the provisional clamp value CLP_a2 calculated in step S412 (CLP_a=CLP_a1+CLP_a2).

Steps S414 and S415 correspond to steps S310 and S311 described above in FIG. 14, respectively.

According to the above-describe second embodiment, the first calculation unit 646 calculates, as a lateral streak noise index, a statistical value of difference image data for each frame generated by the second generation unit 645, the second calculation unit 647 calculates, for each of different correlation degrees between a plurality of dummy pixels 247 and a plurality of unit pixels 230 in each horizontal line, a plurality of lateral streak noise indices calculated by the first calculation unit 646 for each frame, the third calculation unit 648 calculates, as a correction value to correct lateral streak noise included in image data, a correlation degree in which a lateral streak noise index becomes a minimum value among the plurality of lateral streak noise indices calculated by the second calculation unit 647 for each of the different correlation degrees, and the recording control unit 649 records the correction value calculated by the third calculation unit 648 in the eigenvalue information recording unit 531 of the connector recording unit 53 in the endoscope 2. Therefore, even in a case where kinds of noise different from each other are generated in an OB pixel portion and an effective pixel portion due to fluctuation in power supply voltage, lateral streak noise may be corrected in each first chip 21 with accuracy higher than in the above-described first embodiment.

Additionally, according to the second embodiment, since dummy pixel 247 that generates a dummy signal equivalent to an OB pixel shielded from light is used, lateral streak noise may be corrected with high accuracy in each first chip 21 even in a case where an OB pixel needed to calculate a clamp value may not be arranged in a first chip 21, and therefore, the area of the first chip 21 may be reduced. Meanwhile, in the second embodiment, the example in which a dummy pixel 247 that is equivalent to an OB pixel and generates a dummy signal has been described as an example of a correction pixel that outputs a dummy signal, but an OB pixel shielded from light is also applicable.

Furthermore, according to the second embodiment, the average value calculation unit 912 calculates an average value of dummy signals respectively output from a plurality of dummy pixels 247 in an image corresponding to image data acquired by the acquisition unit, the clamp value calculation unit 913 calculates, for each horizontal line, a clamp value to correct respective imaging signals of a plurality of unit pixels 230 based on the average value of the dummy signals respectively output from the plurality of dummy pixels 247 calculated by the average value calculation unit 912, a range of horizontal lines in the imaging unit 20, and a coefficient, and the correction unit 914 corrects respective imaging signals of the plurality of unit pixels 230 in a horizontal line to be corrected based on the clamp value calculated by the clamp value calculation unit 913 for each horizontal line. Therefore, even in a case where kinds of noise different from each other are generated in an OB pixel portion and an effective pixel portion respectively due to fluctuation in power supply voltage, lateral streak noise may be corrected in each first chip 21 with accuracy higher than in the above-described first embodiment.

Modified Example of Second Embodiment

In the second embodiment, the coefficient k1 used to correct lateral streak noise satisfies the condition of 0 k1≤1 and the condition k2 satisfies the condition of 0 k2≤1, but a following condition (5) may also be satisfied.

$$k1+k2=1 \quad (5)$$

In this case, Expression (6) below is established in the seventh calculation unit 643c based on above-described Expressions (2) to (4).

$$CLP\_a(n)=(CLP\_temp1(n,m1))\times k1+(CLP\_temp2(n,m2))\times k2 \quad (6)$$

Therefore, Expression (7) below is established based on the above-described condition (5).

$$CLP\_a(n)=(CLP\_temp1(n,m1))\times k1+(CLP\_temp2(n,m2))\times(1-k1) \quad (7)$$

Thus, when the condition (5) is satisfied, the seventh calculation unit 643c does not need AVE_ob in calculating a clamp value CLP_a(n) because of Expression (7) described above, and therefore, it is not necessary to make the recording unit 63 or the like preliminarily record output (dummy signals) of all of dummy pixels 247 (OB pixels) included in a frame. As a result, memory capacity of the recording unit 63 may be reduced, and output delay of image data caused by correction processing may be suppressed. Furthermore, since the image processing unit 64 may practically reduce one parameter from the total number of parameters required for correction processing, the correction processing may be speeded up.

According to the above-described modified example of the second embodiment, there is no need to store image data for one frame, and therefore, output delay of image data caused by the correction processing may be suppressed.

OTHER EMBODIMENTS

Meanwhile, in the present embodiments, an image processing unit 64 is provided inside an inspection device 6, but may be provided in a connector portion 5 of an endoscope 2 or an operating unit 4 of the endoscope 2.

Additionally, in the present embodiments, an image processing unit 91 is provided inside a processor 9, but may be provided in the connector portion 5 of an endoscope 2 or an operating unit 4 of the endoscope 2.

Furthermore, in the present embodiments, an eigenvalue information recording unit 531 is provided inside the connector portion 5 of the endoscope 2, but may be provided inside a first chip 21 or may be provided inside the operating unit 4.

Meanwhile, in the present embodiments, an endoscope to be inserted into a subject is applied, but for example, a capsule-shaped endoscope or an imaging device adapted to image a subject may also be applicable.

Meanwhile, wordings such as "first", "after that", and "subsequently" are used to clarify anteroposterior relations in the processing between steps in the description of flowcharts in the present specification, but note that the processing order required to implement the present disclosure is not uniquely determined by these wordings. In other words, the processing order disclosed in the flowcharts of the present specification may be changeable within a range having no contradiction.

According to the present disclosure, there is an effect that lateral streak noise may be corrected with high accuracy even in a case where kinds of noise different from each other are generated in an OB pixel portion and an effective pixel portion due to fluctuation in power supply voltage.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An inspection device for calculating a correction value to correct lateral streak noise included in image data generated by an imaging element that includes: a plurality of effective pixels arranged in a two-dimensional matrix, each receiving light from outside, and generating and outputting an imaging signal in accordance with a received light amount; and one or a plurality of correction pixels provided in each horizontal line in arrangement of the plurality of effective pixels, and generating and outputting a dummy signal used in correction processing for the imaging signal, the inspection device comprising:
    an acquisition unit configured to acquire, from the imaging element, a plurality of pieces of dark-time image data generated by the imaging element in a state where the imaging element is shielded from light;
    a first generation unit configured to generate average added image data by adding up the plurality of pieces of dark-time image data acquired by the acquisition unit and dividing the added-up result by number of frames of the dark-time image data;
    a second generation unit configured to generate, for each frame, difference image data in which the average added image data generated by the first generation unit is subtracted from the image data corrected based on a correlation degree between the plurality of correction pixels and the plurality of effective pixels in each horizontal line;
    a first calculation unit configured to calculate, as a lateral streak noise index, a statistical value of the difference image data generated by the second generation unit for each frame;
    a second calculation unit configured to calculate, for each correlation degree, a plurality of the lateral streak noise indices calculated by the first calculation unit for each frame;
    a third calculation unit configured to calculate, as the correction value, the correlation degree having a minimum value among the plurality of the lateral streak noise indices calculated by the second calculation unit for each correlation degree; and
    a recording control unit configured to record the correction value calculated by the third calculation unit in a recording unit provided in the imaging element.

2. The inspection device according to claim 1, further comprising:
    a fourth calculation unit configured to calculate, for each horizontal line, a clamp value to correct the imaging signal of each of the plurality of effective pixels based on the correlation degree; and
    a clamp processing unit configured to perform, for each horizontal line, clamp processing to subtract the clamp value calculated by the fourth calculation unit from the imaging signal of each of the plurality of effective pixels,
    wherein the second generation unit generates, for each frame, the difference image data by subtracting the average added image data generated by the first generation unit from the image data applied with the clamp processing by the clamp processing unit.

3. The inspection device according to claim 2, wherein
    the first calculation unit calculates, for each horizontal line, an average value of the imaging signals of a difference image corresponding to the difference image data generated by the second generation unit, and
    the second calculation unit calculates, as the lateral streak noise index for each frame, a statistical value based on the average value of the imaging signals calculated by the first calculation unit for each horizontal line.

4. The inspection device according to claim 2 wherein the fourth calculation unit includes:
    a fifth calculation unit configured to calculate, for each frame, an average value of dummy signals output from the respective correction pixels in dark-time image corresponding to the dark-time image data acquired by the acquisition unit;
    a sixth calculation unit configured to calculate an average value of dummy signals output from the respective correction pixels in a range of horizontal lines which include a horizontal line to be corrected in the dark-time image corresponding to the dark-time image data acquired by the acquisition unit and are located in vertical direction while setting the horizontal line as a reference; and
    a seventh calculation unit configured to calculate CLP_a (n) by Expression (1) below in a case where a horizontal line to be corrected is defined as n, the range is defined as m, an average value of dummy signals output from the respective correction pixels of the dark-time image is defined as AVE_ob, an average value of dummy signals output from the respective correction pixels in the range is defined as CLP_temp (n, m), a coefficient indicating the correlation degree is defined as k, and the clamp value is defined as CLP_a(n):

$$CLP\_a(n)=(CLP\_\text{temp}(n,m)-AVE\_ob) \times k + AVE\_ob \quad (1)$$

Here, k satisfies $0 \leq k \leq 1$.

5. The inspection device according to claim 2, wherein the fourth calculation unit includes:
   a fifth calculation unit configured to calculate, for each frame, an average value of dummy signals output from the respective correction pixels in dark-time image corresponding to the dark-time image data acquired by the acquisition unit;
   a sixth calculation unit configured to calculate an average value of dummy signals output from the respective correction pixels in a range of horizontal lines which include a horizontal line to be corrected in the dark-time image corresponding to the dark-time image data acquired by the acquisition unit and are located in vertical direction while setting the horizontal line as a reference; and
   a seventh calculation unit configured to calculate CLP_a(n) by Expressions (2) to (4) below in a case where a horizontal line to be corrected is defined as n, the ranges different from each other are defined as m1 and m2, an average value of dummy signals output from the respective correction pixels of the dark-time image is defined as AVE_ob, average values of dummy signals output from the respective correction pixels in the ranges different from each other are defined as CLP_temp1(n, m1) and CLP_temp2(n, m2), coefficients indicating the correlation degrees different from each other are defined as k1 and k2, and the clamp value is defined as CLP_a(n):

$$CLP\_a1(n)=(CLP\_\text{temp}1(n,m1)-AVE\_ob) \times k1 + (AVE\_ob \times 2) \quad (2)$$

$$CLP\_a2(n)=(CLP\_\text{temp}2(n,m2)-AVE\_ob) \times k2 + (AVE\_ob \times 2) \quad (3)$$

$$CLP\_a(n)=CLP\_a1(n)+CLP\_a2(n) \quad (4)$$

Here, k1 satisfies a condition of $0 \leq k1 \leq 1$, and k2 satisfies a condition of $0 \leq k2 \leq 1$.

6. The inspection device according to claim 5, wherein the k1 and k2 satisfy a condition (5) below:

$$k1+k2=1 \quad (5).$$

7. The inspection device according to claim 1, wherein the correlation degree is a difference between a dummy signal output from each of the plurality of correction pixels and an imaging signal output from each of the plurality of effective pixels in each horizontal line.

8. The inspection device according to claim 1, wherein the statistical value is a standard deviation.

9. The inspection device according to claim 1, wherein the correction pixel is a dummy pixel equivalent to an OB pixel shielded from light and generating a dummy signal.

10. The inspection device according to claim 1, wherein the correction pixel is an OB pixel shielded from light.

11. The inspection device according to claim 1, wherein the imaging element is arranged at a distal end of an inserting portion of an endoscope that images a subject, and
   the recording unit is formed continuous from the inserting portion and arranged inside a connector portion connectable to a processor that applies image processing to the image data.

12. A correction value calculating method executed by an inspection device that calculates a correction value used in correcting lateral streak noise included in image data generated by an imaging element including: a plurality of effective pixels arranged in a two-dimensional matrix, each receiving light from outside, and generating and outputting an imaging signal in accordance with a received light amount; and one or a plurality of correction pixels provided in each horizontal line in arrangement of the plurality of effective pixels, and generating and outputting a dummy signal used in correction processing for the imaging signal, the method comprising:
   acquiring, from the imaging element, a plurality of pieces of dark-time image data generated by the imaging element in a state where the imaging element is shielded from light;
   first generating average added image data by adding up the plurality of pieces of dark-time image data acquired in the acquiring step, and then dividing the added-up result by number of frames of the dark-time image data;
   secondly generating, for each frame, difference image data in which the average added image data generated in the first generating step is subtracted from the image data corrected based on a correlation degree between the correction pixel and the plurality of effective pixels in each horizontal line;
   first calculating, as a lateral streak noise index, a statistical value of the difference image data generated for each frame in the second generating step;
   secondly calculating, for each correlation degree, a plurality of the lateral streak noise indices calculated in the first calculating step for each frame;
   thirdly calculating, as the correction value, a correlation degree having a minimum value among the plurality of the lateral streak noise indices calculated in the second calculating step for each correlation degree; and
   performing recording control to record the correction value calculated in the third calculating step in a recording unit provided in the imaging element.

13. A non-transitory computer-readable recording medium on which an executable program for an inspection device that calculates a correction value used in correcting lateral streak noise included in image data generated by an imaging element including: a plurality of effective pixels arranged in a two-dimensional matrix, each receiving light from outside, and generating and outputting an imaging signal in accordance with a received light amount; and one or a plurality of correction pixels provided in each horizontal line in arrangement of the plurality of effective pixels, and generating and outputting a dummy signal used in correction processing for the imaging signal is recorded, the program instructing a processor of the inspection device to execute:
   acquiring, from the imaging element, a plurality of pieces of dark-time image data generated by the imaging element in a state where the imaging element is shielded from light;
   first generating average added image data by adding up the plurality of pieces of dark-time image data acquired in the acquiring step, and then dividing the added-up result by number of frames of the dark-time image data;
   secondly generating, for each frame, difference image data in which the average added image data generated by the first generating step is subtracted from the image data corrected based on a correlation degree between the correction pixel and the plurality of effective pixels in each horizontal line;

first calculating, as a lateral streak noise index, a statistical value of the difference image data generated in the second generating step for each frame;

secondly calculating, for each correlation degree, a plurality of the lateral streak noise indices calculated in the first calculating step for each frame;

thirdly calculating, as the correction value, the correlation degree having a minimum value among the plurality of the lateral streak noise indices calculated in the second calculating step for each correlation degree; and performing recording control to record, in a recording unit provided in the imaging element, the correction value calculated in the third calculating step.

\* \* \* \* \*